United States Patent
Guo et al.

(10) Patent No.: US 8,071,637 B2
(45) Date of Patent: Dec. 6, 2011

(54) DITHIOLOPYRROLONES COMPOUNDS AND THEIR THERAPEUTIC APPLICATIONS

(75) Inventors: Yingping Guo, Burnaby (CA); Genhui Chen, Burnaby (CA); Bin Li, Burnaby (CA)

(73) Assignee: Welichem Biotech Inc., Burnaby (CA)

( * ) Notice: Subject to any disclaimer, the term of this patent is extended or adjusted under 35 U.S.C. 154(b) by 129 days.

(21) Appl. No.: 12/440,331

(22) PCT Filed: Sep. 10, 2007

(86) PCT No.: PCT/IB2007/053641
§ 371 (c)(1),
(2), (4) Date: Aug. 11, 2009

(87) PCT Pub. No.: WO2008/038175
PCT Pub. Date: Apr. 3, 2008

(65) Prior Publication Data
US 2010/0041729 A1    Feb. 18, 2010

Related U.S. Application Data

(60) Provisional application No. 60/847,919, filed on Sep. 29, 2006.

(51) Int. Cl.
*C07D 513/04*    (2006.01)
*A61K 31/407*    (2006.01)

(52) U.S. Cl. ........................................ 514/412; 548/453

(58) Field of Classification Search ........................ None
See application file for complete search history.

(56) References Cited

FOREIGN PATENT DOCUMENTS

| | | | |
|---|---|---|---|
| GB | 2 170 498 A | 8/1986 |
| JP | 63-284181 A | 11/1988 |
| JP | 11-279179 A | 10/1999 |
| WO | WO 95/05384 A1 | 2/1995 |
| WO | WO 99/12543 A1 | 3/1999 |
| WO | WO 03/086024 A1 | 10/2003 |

OTHER PUBLICATIONS

Athens, John W., "Neutropenia", Wintrobe's Clinical Hematology, Ed. Richard G. Lee, USA: Lippincott, Williams and Wilkins, 1993, 1589-1612.

Bhate, D.S. and Y.M. Sambray, "Synthetic thiolutin analogues", Hindustan, Antibiotic Bulletin, 6(1):17-18, 1963.

Hagio, Katsuaki, et al. "Total synthesis of holomycin, thiolutin, and aureothricin", Bulletin of the Chemical Society of Japan, 47(6):1484-1489, 1974.

Oyesanmi, Olu, et al. "Hematologic side effects of psychotropics", Psychosomatics, 40(5): 414-421, Sep.-Oct. 1999.

van der Klauw, Melanie M., et al. "A population-based case-cohort study of drug-associated agranulocytosis", Arch Interm Med, 159(4):369-374, Feb. 22, 1999.

Sharma, S., et al., "Screening of potential chemopreventive agents using biochemical markers of carcinogenesis", Cancer Research, 1994, 54, 5848-5855.

Celmer, W.D. and I.A. Solomons. Antibiotics Annual 1953-1954, Medical Encyclopedia, Inc., New York, p. 622-625, (1953).

Ellis, John E., et al., "Synthesis of Holomycin and Derivatives", J. Org. Chem., 1977, 42(17):2891-2893.

*Primary Examiner* — Yong Chu
*Assistant Examiner* — Michael Barker
(74) *Attorney, Agent, or Firm* — Oyen Wiggs Green & Mutala LLP

(57) ABSTRACT

The present invention provides dithiolopyrrolone compounds of the general formula I, and their salts, wherein A is sulfur or carbon, and $R_1$, $R_2$, and $R_3$ are selected from groups defined herein, and wherein when A is sulfur, then B is oxygen, and n=1 or 2, and when A is carbon, then B is oxygen or sulfur, and n=1. The compounds are useful for the prevention and treatment of microbial infections such as HIV infection, and for the treatment of blood disorders, such as neutropenia. In particular, the compounds are useful for the manufacture of medicaments for increasing white blood cells.

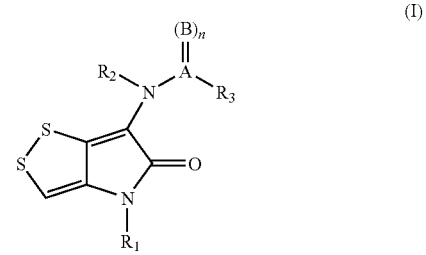

12 Claims, No Drawings

DITHIOLOPYRROLONES COMPOUNDS AND THEIR THERAPEUTIC APPLICATIONS

The present invention provides novel dithiolopyrrolone compounds and their salts, which promote production of white blood cells and are useful as prevention and treatments for microbial infections such as HIV infection and blood disorders such as neutropenia and other related diseases. The present invention also provides therapeutic compositions comprising particularly useful types of dithiolopyrrolones, the salts thereof, and methods and use in the manufacture of a medication for treatment of diseases.

BACKGROUND OF THE INVENTION

The human blood-forming (hematopoietic) system is comprised of a variety of white blood cells (including neutrophils, macrophages, basophils, mast cells, eosinophils, T and B cells), red blood cells (erythrocytes) and clot-forming cells (megakaryocytes, platelets).

It is understood that certain hematopoietic growth factors such as chemicals and proteins naturally occurring inside animals are responsible for the differentiation of a small number of "stem cells" into a variety of blood cell progenitors for the tremendous proliferation of those cells, and for the ultimate differentiation of mature blood cells from those lines. The hematopoietic regenerative system functions well under normal conditions. However, when stressed by chemotherapy, radiation, or natural myelodysplastic disorders, a resulting period during which patients are seriously leukopenic, anemic, or thrombocytopenic occurs. Neutropenia is an abnormally low level of neutrophils in the blood. Neutrophils are white blood cells (WBCs) produced in the bone marrow and comprise approximately 60% of the blood. These cells are critically important to an immune response and migrate from the blood to tissues during an infection. They ingest and destroy particles and germs. Germs are microorganisms such as bacteria, protozoa, viruses, and fungus that cause diseases. Neutropenia is an especially serious disorder for cancer patients who may have reduced immune functions because it makes the body vulnerable to viral, bacterial and fungal infections. White blood cells are especially sensitive to chemotherapy. The number of cells killed during radiation therapy and chemotherapy depends upon the dose and frequency of the treatment.

Neutropenia is a blood disorder wherein the number of neutrophils in the blood is abnormally low as assessed by an Absolute Neutrophil Count (ANC). A neutrophil shortage corresponds to an increased risk of microbial infection. The blood of healthy human adults contains about 2500 to 6000 neutrophils per $mm^3$. In children under the age of six, the count may be lower. Various sources have set the threshold for the diagnosis of neutropenia at different measured neutrophil levels ranging from an ANC of about 2000 neutrophils per $mm^3$ to about 1500 neutrophils per $mm^3$. See The Merck Manual $18^{th}$ Ed. 2006, Section 11, the entire disclosures of which are incorporated herein by reference. Severe neutropenia is diagnosed when the ANC falls below 500 neutrophils per $mm^3$. The symptoms, of increased risk of infection depend on the severity of the neutropenia and on the duration of the disorder.

Neutropenia treatable by compounds and methods of the present invention may be a chronic disorder. Neutropenia as a chronic disorder may be further classified as congenital, cyclical and idiopathic neutropenia. Chronic congenital neutropenia is inherited by a small number of individuals. The most severe form of congenital neutropenia is Kostmann's Syndrome and there are other, milder variations. Symptoms include frequent infections and fevers.

Cyclical neutropenia results from a regulatory defect at the hematopoietic stem cell level that causes oscillations in production of neutrophils as well as other types of blood cells. Individuals with this disorder will have neutrophil counts of about 100 neutrophils per $mm^3$ for three to six days out of every cycle. The neutrophil count ranges from severe to moderate neutropenia levels through most of the cycle.

Chronic idiopathic neutropenia refers to severe chronic neutropenia that does not clearly fall into either of the above classifications. Individuals suffering from chronic idiopathic neutropenia typically acquire the disorder after having normal neutrophil counts earlier in life. It is estimated that neutropenia may occur as a congenital or idiopathic disorder in an estimated frequency of one per 200,000 in the population.

Neutropenia may also be occurred secondary to another condition such as cancer or Acquired Immunodeficiency Syndrome (AIDS). Neutropenia may also be occurred secondary to an event such as a drug therapy. Thus, neutropenia may result from physiological disorders that directly affect the immune system. For example, diminished neutrophil production will be resulted when leukemia, myeloma, lymphoma or a metastatic solid tumor such as, for example, breast or prostate cancer, infiltrate and replace bone marrow. Transient neutropenia is often associated with viral infections. Chronic neutropenia is often associated with immunodeficiency resulting from a viral infection, for example, AIDS resulting from infection with Human Immunodeficiency Virus (HIV). Autoimmune neutropenia may be associated with circulating antineutrophil antibodies.

A much more common cause is neutropenia as a side effect of drug therapy, particularly cancer chemotherapy, radiation therapy for cancer and bone marrow transplantation associated with cancer therapy. Neutropenia secondary to drug therapy can thus be subdivided into two groups. The first involves immune-mediated neutropenia that may arise from drugs that act as haptens to stimulate antibody formation. Acute hypersensitivity reactions such as those caused by diphenylhydantoin and phenobarbital may last a few days. However, chronic hypersensitivity reactions may last for months or years. See The Merck Manual, $18^{th}$ Ed.

The second area of drug-induced neutropenia involves the severe neutropenia that predictably occurs after large doses of cytoreductive cancer drugs and which also accompanies ionizing radiation therapy. These cytotoxic therapies induce neutropenia because of the proliferative nature of neutrophil precursor cells and the normal rapid turnover rate of circulating neutrophils. See The Merck Manual, $18^{th}$ Ed. The risk of neutropenia secondary to cancer chemotherapy or radiotherapy depends on the type and stage of the cancer and the type, the dosage and the schedule of cancer treatment. Each year over 1.5 million cancer patients in the US received chemotherapy. About one half of chemotherapy patients develop neutropenia. At present, less than 10% of chemotherapy patients receive prophylactic treatment to prevent neutropenia.

Therapy that exists currently for hematopoietic disorders include the use of proteineous hematopoietic factors such as EPO, G-CSF, GM-CSF, CSF-1, IL-1, IL-2, IL-3, IL-4, IL-5, IL-6, IL-7, IL-8, IL-9, IL-10, IL-11, IGF-I, or LIF (Leukemic Inhibitory Factor) and other chemicals. Therapy for raising neutrophil levels consists primarily of filgrastim (Nupogen®) and more recently, pegfilgrastim (Neulasta™), a longer acting derivative of filgrastim. Filgrastim is a recombinant version of a human protein, G-CSF (granulocyte-colony stimulating factor), that selectively stimulates the production of white blood cells. G-CSF is currently the drug of choice for neutropenia. Since both of these drugs are recombinant proteins they are not active orally and must be administered by injection. In addition, protein-based drugs are often subject to rapid metabolism.

New agents, in particular, non protein-based drugs are needed which are useful in the treatment of neutropenia. In particular, agents are needed that demonstrate biological activity when administered via routes other than injection. Particularly, agents that may be orally active are needed, as they may serve to enhance patient compliance.

Dithiolopyrrolones are a group of compounds with 1,2-dithiolo[4,3-b]pyrrol-5(4H)-one ring. Compounds bearing this basic structural feature have been known in the art with a broad range of activities, including antimicrobial, chemopreventive (Sharma et al., 1994) and anticancer (WO 99/12543, WO2003/080624, both of Webster et al.). However, the surprising, novel activities of increasing white blood cells in animals was not known until now. Certain synthetic dithiolopyrrolones and their antimicrobial activities have been disclosed (D. S. Bhate & Y. M. Sambray, 1963. Hindustan, *Antibiotic Bulletin* 6(1): 17-18; Katsuaki Hagio et al. *Bull. Chem. Soc. Jpn* 1974, 47, 1484-1489; Broom et al. WO 9505384 and Godfrey & Dell, GB2170498, Webster et al. WO 99/12543, WO2003/080624).

The present invention relates to new dithiolopyrrolones, to their novel activities in increasing white blood cells and their use in promoting white blood cells, in preventing and treatment of microbial infections and of blood disorders such as neutropenia.

SUMMARY OF THE INVENTION

In one aspect the invention provides methods and compositions for treating blood disorders, such as neutropenia, comprising administrating to a subject in need of such treatment, an effective amount of a compound of one of the compounds of the present invention. In another aspect, the invention deals with pharmaceutical compositions containing compounds of the structures shown below. In another aspect, the invention includes, novel chemical compounds of the structures shown in formula I below.

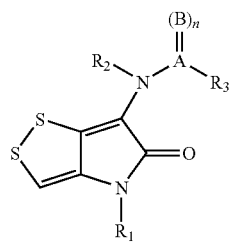

Formula I

In this disclosure, dithiolopyrrolones within the Formulae I, are referred to as "types of dithiolopyrrolones" according to the invention or by similar wording, and individual compounds disclosed herein are referred to by the wording "specific dithiolopyrrolones", "specific compounds", "particular compounds" or "compounds of the invention" or by similar wording.

The phrase "effective amount" when used to describe therapy to an individual refers to an amount of a compound of formula I which results in increasing white blood cells, in particular, neutrophil production as measured by the absolute neutrophil count of the individual's blood. An effective amount of a compound of formula I for prevention and treatment of microbial infection and neutropenia is an amount which raises the absolute neutrophil count in an individual afflicted. An effective amount of a compound of formula I for the prevention of neutropenia is an amount which maintains the absolute neutrophil count of the individual above a level of about 500 neutrophils per $mm^3$ in an individual during a time interval coinciding with an increased risk of neutropenia. Conditions which are associated with an increased risk of neutropenia include, for example, a present or forthcoming regimen of cancer chemotherapy.

The term "individual" or "subject," includes human beings and non-human animals. With respect to the disclosed methods of increasing white blood cell (neutrophil) production, these terms refer, unless the context indicates otherwise, to: (a) an organism that is afflicted with a disorder characterized by low WBC, including neutropenia; or (b) an organism that is at increased risk for developing neutropenia, due, for example, to forthcoming cancer chemotherapy. The selection of an individual at increased risk for developing neutropenia may take into account the presence of known risk factors. Such factors may include, for example, cancer requiring chemotherapy or therapeutic ionizing radiation; a disease that affects the immune system directly, such as for example AIDS; or the presence of a virus such as HIV known to cause AIDS.

DETAILED DESCRIPTION OF THE INVENTION

According to the present invention, dithiopyrrolones of formula I, and pharmaceutically-acceptable salts thereof, may be used to increase WBC, in particular, neutrophil levels in an individual as measured by a blood account.

The dithiolopyrrolones of formula I useful in the present invention may be prepared by one of several methods. These methods generally follow the synthetic strategies and procedures used in the synthesis of these disclosed by Webster et al. (WO2003/080624) and references cited therein, the entire disclosures of which are incorporated herein by reference.

The types of dithiolopyrrolones and specific dithiolopyrrolones of the subject invention are prepared by the methods described below together with the structure of each dithiolopyrrolone compound for which structural information is given and has been confirmed by its NMR and MS spectroscopy.

Skilled chemists will be able to use procedures as disclosed herein and others to produce these types of dithiolopyrrolones and specific dithiolopyrrolones from commercially available stock substances. In carrying out such operations, any suitable filtration, chromatographic, and other purification techniques might be employed by those skilled in the art. A more complete understanding of the invention can be obtained by reference to preferred embodiments of the invention, which are illustrated by the following specific examples and methods of the invention. It will be apparent to those skilled in the art that the examples involve use of materials and reagents that are commercially available from chemical companies, so no details are given respecting them.

The compounds used in the methods of the present invention may take the form of pharmaceutically-acceptable salts. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Suitable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable base addition salts of compounds of formula I useful in methods of the invention include for example, metallic salts made from calcium, magnesium, potassium, sodium and zinc or organic salts made from chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The use of compounds of formula I to raise WBC levels may be associated with one or more of several therapeutic goals. Therapy to raise WBC levels may treat WBC-related disorders, such as neutropenia that exists as a primary disease state. Alternatively, therapy according to use and methods of the invention may treat disorders that are secondary to another factor. Such factors include, for example, microbial infections, cancer or therapy with a drug that causes these conditions. Microbial infections include those caused by viruses, bacteria and fungi.

Therapy to raise WBC levels by methods of the present invention may also prevent neutropenia in instances wherein an individual is at risk of developing neutropenia. Such instances include, for example, an individual who anticipates beginning drug therapy using a drug known or suspected to cause neutropenia.

Numerous drugs have been shown to cause neutropenia as a side effect. Such side effects have been observed in drugs in a variety of drug classes including, for example, thyroid inhibitors, antibiotics, neuropsychotropics, cardiovascular medications, analgesics, antimalarials, nonsteroidal antiinflammatory agents, antihistamines and combinations thereof. See Lee, Wintrobe's Hematology, Lippincott, p. 1862-1869, and van der Klauw, M. M et al., *Arch. Intern. Med.*, 1999, 159 (4), the entire disclosure of which is incorporated herein by reference. Neutropenia induced by any of the aforementioned drugs may be treated or prevented according to the present invention.

A more common source of drug-induced neutropenia involves the severe neutropenia that predictably occurs after large doses of cytoreductive cancer drugs and which also accompanies ionizing radiation therapy. The predictability of neutropenia in an individual undergoing chemotherapy for cancer provides a basis for methods of the present invention for providing prophylactic administration. See The Merck Manual, 18$^{th}$ Ed., 2006, Section 11 "Hematology and Oncology", the entire disclosure of which is incorporated herein by reference.

The compounds useful in methods of the invention may be administered to individuals (mammals, including animals and humans) for treatment or prevention of reduction of white blood cells and related disorders such as neutropenia.

Instances wherein neutropenia may be prevented include administration to individuals receiving cancer chemotherapy or to individuals in preparation for imminent cancer chemotherapy. Methods of the invention also include administration to an individual in association with, or in preparation for other events that have been shown to increase the risk of the individual subsequently developing neutropenia. Such factors include, but are not limited to: Therapeutic radiation therapy; drug therapies other than cancer chemotherapy wherein the individual is known or suspected to have a sensitivity to the therapy that increases the risk of developing neutropenia; drug therapies other than cancer chemotherapy wherein the drug is associated with a high incidence of neutropenia, an immunodeficiency such as AIDS; or a virus known to cause immunodeficiency, such as for example HIV.

The compounds useful in use of the invention may be administered to individuals (mammals, including animals and humans) for treatment of reduction of white blood cells to prevent or treat microbial infections. It is known that one of the main functions of white blood cells is fighting microbial infections, such as virus, bacteria and fungi. The activity of increasing white blood cells finds use and utility in prevention and treatment of microbial infections. Skilled practioners will be able to use procedures that might be employed by those skilled in the art. See The Merck Manual, 18$^{th}$ Ed., 2006, the entire disclosure of which is incorporated herein by reference.

The present invention also relates to the pharmaceutical compositions which contain an active ingredient of these compounds or a pharmaceutically acceptable salt thereof, or a compound or pharmaceutically acceptable salt selected from a type of dithiolopyrrolone of the invention, as well as the process for the preparation of such a pharmaceutical composition.

Examples of pharmaceutical compositions include any solid (tablets, pills, capsules, granules, powder etc.) or liquid (solutions, suspensions or emulsions) in a suitable composition for oral, topical or parenteral administration. These formulations may contain the pure compound, or the salt thereof or be in combination with a carrier or some other pharmaceutically active compound. These compositions may need to be sterile when administered parenterally.

For treating or preventing infection and neutropenia, the specific dose of compound according to the invention to obtain therapeutic benefit will be determined by the particular circumstances of the individual patient including, the size, weight, age and sex of the patient. Also determinative will be the nature and stage of the disease and the route of administration. For example, a daily dosage of from about 100 to 1500 mg/day may be utilized. Preferably, a daily dosage of from about 100 to 1000 mg/day may be utilized. More preferably, a daily dosage of from about 100 to 500 mg/day may be utilized. Higher or lower doses are also contemplated. Neutrophil levels may be monitored in the patient and the treatment regimen may be maintained until neutrophil levels reach a normal range.

For preventive administration, the compounds useful in the practice of methods of the invention should be administered far enough in advance of a known event that increases the risk of neutropenia such that the compound is able to reach the site of action in sufficient concentration to exert therapeutic effect. The pharmacokinetics of specific compounds may be determined by means known in the art and tissue levels of a compound in a particular individual may be determined by conventional analyses.

One or more compounds useful in the practice of the present inventions may be administered simultaneously, or different dithiopyrrolones useful in the practice of the present invention may be administered at different times during treatment or prevention therapy.

The methods of the present invention may comprise administering compounds of the present invention in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient that is compatible with the other ingredients of the formulation and to deleterious to the recipient.

The compounds useful in methods of the invention may be administered for therapeutic effect by any route, for example enteral (e.g., oral, rectal, intranasal, topical, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For use to increase WBC such as neutrophil levels, the drug may be localized in a depot for controlled release to the circulation.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a pharmaceutically-acceptable water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention can also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

The controlled-release of the active ingredient can be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient or a pharmaceutically-acceptable salt thereof) in the pharmaceutical composition. In another embodiment, the controlled-release component is biodegradable, induced by exposure to the aqueous environment, pH, temperature, or enzymes in the body. In another embodiment, sol-gels can be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The practice of the invention is illustrated by the following non-limiting examples.

EXAMPLE 1

Activity of Increasing White Blood Cells (WBC) in Mice

This activity was determined using CDF1 male mice (18-20 g): mice were grouped as: vehicle, 30 mg/kg cyclophosphamide (CTX), 15 mg/kg test compounds. The mice were treated by IP injection: test compounds on day 1, 3, and 5 for three doses, vehicle and CTX daily for 6 days. On day 7, peripheral blood samples were collected and blood cells counted.

Results: 0058 significantly increased white blood accounts in dogs with a clear dose response (Table 2).

TABLE 1

Effect on mouse peripheral white blood cells

| Group | N | WBC ($\times 10^9$/L) |
|---|---|---|
| Vehicle | 14 | 4.1 ± 0.9 |
| 0058 | 13 | 23.9 ± 8.9 |
| 0227 | 13 | 13.7 ± 3.1 |
| 0230 | 13 | 11.3 ± 2.6 |
| 0249 | 13 | 18.2 ± 1.8 |
| 0253 | 13 | 10.5 ± 2.3 |
| CTX | 11 | 1.41 ± 0.50 |

EXAMPLE 2

Activity of Increasing WBC in Dogs

The effect of the test compounds was tested on beagle dog with a daily IV injection at different doses for four days. The blood account was done at day 5.

Results: 0058 significantly increased white blood accounts in dogs with a clear dose response (Table 2).

TABLE 2

Effect of 0058 on white blood cells of beagle dog

| Dose (mg/kg) | WBC (×10⁹/L) | % increase* |
|---|---|---|
| 1 | 13.0 ± 2.0 | 15.9 |
| 2 | 16.8 ± 1.0 | 48.2 |
| 4 | 21.5 ± 4.1 | 90.3 |
| 8 | 28.8 ± 7.0 | 154.9 |

*data compared with the control

EXAMPLE 3

Therapeutical Effect on White Blood Cells of Mice

This activity was determined using CDF1 male mice: mice were grouped and treated with daily CTX IP injection of 30 mg/kg for 6 days. The therapeutical treatments started at the $7^{th}$ day when white blood cell account significantly decreased with test compound at 15 mg/kg daily for 3 days. Positive control group was treated with daily subcutaneously injection of 20 μg/kg G-CSF. Peripheral blood samples were collected and blood cells counted on the $10^{th}$ day.

Results: The test compounds have significant therapeutical activity on white blood cells in mice (Table 4).

TABLE 4

Therapeutical effect on white blood cells.

| Group | Day 6 | Day 10 |
|---|---|---|
| Vehicle | 5.1 ± 1.0 | 5.0 ± 0.9 |
| CTX | 1.5 ± 0.2 | 4.8 ± 0.8 |
| G-CSF | 1.8 ± 0.7 | 14.7 ± 1.8 |
| 0058 | 2.1 ± 0.8 | 16.2 ± 2.1 |
| 0227 | 1.6 ± 0.4 | 17.3 ± 1.2 |
| 0230 | 1.7 ± 0.5 | 13.1 ± 1.5 |

Expressed as number of white blood cell account (×10⁹/L).

EXAMPLE 4

Synthesis of Compounds of the Present Invention

The compounds of the present invention are prepared according to the following synthetic scheme (Scheme 1): The compounds of the present invention are prepared according to the following synthetic scheme (Scheme 1):

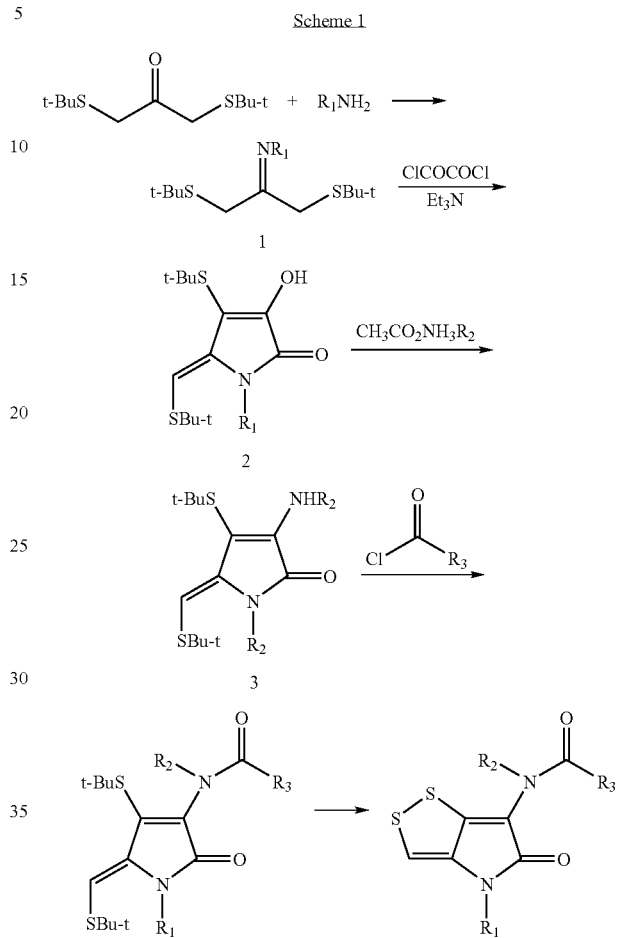

Intermediates prepared according to the above synthetic scheme (Scheme 1) procedure and used for the subsequent syntheses are listed in the following table.

| Intermediate | | $R_1$ | $R_2$ | $R_3$ |
|---|---|---|---|---|
| 1 and 2 | a | 2,4-dimethoxyphenyl | | |
| | b | 1-ethylpyrazole-5-yl | | |
| | c | 3,4,5-trimethoxyphenyl | | |
| | d | benzyl | | |
| | e | phenyl | | |
| | f | 4-methylphenyl | | |
| | g | 4-methoxyphenyl | | |
| | h | 4-isobutylphenyl | | |
| | i | 4-isopropanylphenyl | | |
| | j | methyl | | |
| 3 | a | 2,4-dimethoxyphenyl | H | |
| | b | 1-ethylpyrazole-5-yl | H | |
| | c | 3,4,5-trimethoxyphenyl | H | |
| | d | benzyl | H | |
| | e | phenyl | H | |
| | f | 4-methylphenyl | H | |
| | g | 4-methoxyphenyl | H | |
| | h | 4-isobutylphenyl | H | |
| | i | 4-isopropanylphenyl | H | |
| | j | methyl | H | |

-continued

| Intermediate | | R₁ | R₂ | R₃ |
|---|---|---|---|---|
| | k | H | H | |
| | l | 4-methoxyphenyl | benzyl- | |
| | m | 4-hydroxyphenyl | benzyl- | |
| | n | 2,4-dimethoxyphenyl | methyl | |
| 4 | a | 2,4-dimethoxyphenyl | H | acetyl |
| | b | 2,4-dimethoxyphenyl | H | nicotinoyl |
| | c | 2,4-dimethoxyphenyl | H | trifluoroacetyl |
| | d | 2,4-dimethoxyphenyl | methyl | methyl |
| | e | 2,4-dimethoxyphenyl | methylsulfonyl | methylsulfonyl |
| | f | 2,4-dimethoxyphenyl | 2-thiophenecarbonyl | 2-thiophenecarbonyl |
| | g | 2,4-dimethoxyphenyl | H | α-hydroxyacetyl |
| | h | H | H | nicotinoyl |
| | i | 4-methoxyphenyl | acetyl | acetyl |
| | j | 4-methoxyphenyl | H | trifluoroacetyl |
| | k | 4-methoxyphenyl | trifluoroacetyl | benzyl |
| | l | 4-hydroxyphenyl | trifluoroacetyl | benzyl |
| | m | 3,4,5-trimethoxyphenyl | H | acetyl |
| | n | 4-methylphenyl | H | acetyl |
| | o | 1-ethylpyrazole-5-yl | H | trifluoroacetyl |
| | p | 4-methyhoxyphenyl | H | acetyl |
| | q | 4-isobutylphenyl | H | trifluoroacetyl |
| | r | 4-isopropanylphenyl | H | trifluoroacetyl |
| | s | methyl | H | trifluoroacetyl |
| | t | benzyl | H | trifluoroacetyl |
| | u | 2,4-dimethoxyphenyl | methyl | trifluoroacetyl |

Detailed Synthesis:

Synthesis of compounds 1a-j: To a well stirred solution of 1,3-bis(t-butylthio)-acetone (10 mmol), $R^1NH_2$ (10 mmol) and triethylamine $Et_3N$ (20 mmol) in dry THF (100 ml), a solution of $TiCl_4$ (5.5 mmol) in 15 ml dry hexanes was added dropwise in 30 min at 0-5° C. under $N_2$. After the addition, the reaction mixture was refluxed for 2 hours. Imine compounds so obtained were used for the next step without purification of compound 1.

Synthesis of compounds 2a-j: At –10° C., oxalyl chloride (0.84 ml, 10 mmol) was added to the solution obtained in the previous step. At the same temperature and under stirring, $Et_3N$ (20 mmol) in 100 ml THF was added dropwise in 30 min. Then the solution was stirred at room temperature for 10 hours. The precipitate was filtered and washed with ether (250 ml). The organic solution was washed with water three times and the solvent was evaporated to give a dark brown power. It was recrystallized in ethyl acetate and hexanes to give a light yellow crystal of compound 2. All the compounds 2a-j can be prepared in the same way as described in these two steps. The total yield of these two steps for each of the compounds was about 60-70%.

Synthesis of compounds 3a-k: A 250 ml three neck flask with 50 g ammonium acetate was heated in oil bath under $N_2$ till $NH_4^+OAc^-$ melted. Compound 2 (5 mmol) was added into the flask and the resulting solution was stirred for one hour. The reaction temperature was within 140° C. to 165° C. depending on the proprieties of compound 2. One hour later, the heating was stopped and the reaction mixture was cooled to room temperature. The reaction mixture was dissolved in 100 ml water and extracted with 100 ml ether three times. The extracts were combined, dried over $Na_2SO_4$ and evaporated under reduced pressure. The residue was chromatographed on a column of silica gel to give compound 3. Yields for 3a-i were about 50-60%. Compound 3k was obtained as a by product in the preparations of compound 3a-j and its yields depended on the reaction temperature and length of reaction time.

Synthesis of compounds 3l and 3m: A 150 ml flask with benzylamine acetate 30 g and Compound 2g (2 mmol) was heated to 170° C. under $N_2$. The mixture was stirred at this temperature for about one hour. When it was cooled, 50 ml water was added and it was extracted with 50 ml ether twice. The organic solvent was dried over $Na_2SO_4$ and evaporated under reduced pressure. The residue was purified with silica gel. Two compounds 3l and 3m were obtained with yields 25% and 15% respectively.

Synthesis of compounds 3n: A 100 ml flask with methylamine acetate 20 g and compound 2a (1 mmol) was heated to 170° C. under $N_2$. The mixture was stirred at this temperature for about one hour. When it was cooled, 50 ml water was added and it was extracted with 50 ml ether twice. The organic solvent was dried over $Na_2SO_4$ and evaporated under reduced pressure. The residue was purified with silica gel. 3n was obtained with yields of 40%.

Synthesis of 4a: To a well-stirred solution of 200 mg (0.474 mmol) of 3a in 10 ml of acetic anhydride, 20 mg of concentrated $H_2SO_4$ was added. Half a hour later, the solution was transferred on to a column of silica gel and developed with 200 ml $CH_2Cl_2$ then 500 ml of 20% ether in $CH_2Cl_2$ to give 4a 190 mg (0.41 mmol, 86%).

Synthesis of 4b: A solution of 3a 100 mg (0.24 mmol), nicotinoyl chloride hydrochloride 200 mg (1.12 mmol), and triethylamine 250 mg (2.47 mmol), in 10 ml THF was stirred for 24 hours at room temperature. Afterwards 50 ml of ether was added and the solution was washed with water three times. After it was dried over $Na_2SO_4$, the solvent was evaporated and the residue was purified on a column of silica gel to give 4b 90 mg (0.171 mmol, 72%).

Synthesis of 4c: To a solution of 3a 100 mg (0.24 mmol) in 5 ml of dichloromethane, 300 mg of trifluoroacetic anhydride was added. The resulting solution was stirred for half an hour and then the solvent was evaporated under reduced pressure to give 4c 122 mg (0.237 mmol, 100%).

Synthesis of 4d: In 5 ml of acetonitrile 211 mg 3a (0.5 mmol), 1 ml of formalin was mixed with 100 mg NaCNBH$_3$. While stirring, 0.1 ml glacial acetic acid was added dropwise over 30 minutes. This reaction mixture was stirred for 4 hours and another 0.1 ml glacial acetic acid was added in the middle of the course. It was diluted with 50 ml of ether and extracted with 1N NaOH, as well as with water. After it was dried and evaporated in a vacuum, the residue was chromatographed on a column of silica gel, 150 mg (0.33 mmol) of 4d was obtained in 67% yield.

Synthesis of 4e: To a solution of 3a 100 mg (0.24 mmol) and methylsulfonyl chloride 300 mg in 5 ml of dry THF, 300 mg of triethylamine was added drop by drop at room temperature in one minute. This solution was stirred for half an hour and 50 ml of ether was added and the solution was washed with water three times. After it was dried over Na$_2$SO$_4$, the solvent was evaporated and the residue was chormatographed on a column of silica gel to give 4e 110 mg (0.19 mmol, 80%).

Synthesis of 4f: A solution of 3a 100 mg (0.24 mmol), 2-thiophenecarbonyl chloride 200 mg (1.37 mmol) and trimethylamime 200 mg (1.98 mmol) in 10 ml of THF was refluxed for 10 hours. Afterwards 50 ml of ether was added and the solution was washed with water three times. After it was dried over Na$_2$SO$_4$, the solvent was evaporated and the residue was chromatographed on a column of silica gel to give 4f 120 mg (0.187 mmol, 79%).

Synthesis of 4g: A solution of 3a 100 mg (0.24 mmol), acetoxyacetyl chloride 118 mg (1.0 mmol) and triethylamine 120 mg (1.19 mmol), in 10 ml THF was stirred for 24 hours at room temperature. Afterwards 50 ml of ether was added and the solution was washed with water three times. The solvent was evaporated and the residue was dissolved in a solution of 0.1N sodium hydroxide 1 ml in methanol 10 ml. This solution was stirred for 1 hour. After the solvent was evaporated under reduced pressure, the residue was chormatographed on a column of silica gel to give 4g 105 mg (0.22 mmol, 91%).

Synthesis of 4h: A solution of 3j 100 mg (0.35 mmol), nicotinoyl chloride hydrochloride 250 mg (1.40 mmol), and triethylamine 350 mg (3.46 mmol), in 10 ml THF was stirred for 24 hours at room temperature. Afterwards 50 ml of ether was added and the solution was washed with water three times. After it was dried over Na$_2$SO$_4$, the solvent was evaporated and the residue was chormatographed on a column of silica gel to give 4h 100 mg (0.256 mmol, 73%).

Synthesis of 4i: A solution of 3g 100 mg (0.255 mmol), acetyl chloride 100 mg (1.28 mmol) and triethylamine 260 mg (2.56 mmol), in 10 ml THF was stirred at 50° C. for 12 hours. Afterwards 50 ml of ether was added and the solution was washed with water three times. After it was dried over Na$_2$SO$_4$, the solvent was evaporated and the residue was chormatographed on a column of silica gel to give 4i 110 mg (0.231 mmol, 90%).

Synthesis of 4j: To a solution of 3g 100 mg (0.255 mmol) in 5 ml of dichloromethane, 300 mg of trifluoroacetic anhydride was added. The solution was stirred for half a hour and then the solvent was evaporated under reduced pressure to give 4j 125 mg (0.255 mmol, 100%).

Synthesis of 4k: To a solution of 3l 50 mg (0.104 mmol) in 5 ml of dichloromethane, 150 mg of trifluoroacetic anhydride was added. The solution was stirred for half an hour and then the solvent was evaporated under reduced pressure to give 4k 60 mg (0.104 mmol, 100%).

Synthesis of 4l: To a solution of 3m 50 mg (0.107 mmol) in 5 ml of dichloromethane, 200 mg of trifluoroacetic anhydride was added. The solution was stirred for half an hour and then the solvent was evaporated under reduced pressure to give 4l 60 mg (0.107 mmol, 100%).

Synthesis of 4m: A solution of 3c 100 mg (0.22 mmol), acetyl chloride 70 mg (0.9 mmol) and triethylamine 100 mg (0.99 mmol), in 10 ml THF was stirred at room temperature for 24 hours. Afterwards 50 ml of ether was added and the solution was washed with water three times. After it was dried over Na$_2$SO$_4$, the solvent was evaporated and the residue was chormatographed on a column of silica gel to give 4m 80 mg (0.162 mmol, 73%).

Synthesis of 4n: A solution of 3f 100 mg (0.266 mmol), acetyl chloride 70 mg (0.9 mmol) and triethylamine 100 mg (0.99 mmol), in 10 ml THF was stirred at room temperature for 24 hours. Afterwards 50 ml of ether was added and the solution was washed with water three times. After it was dried over Na$_2$SO$_4$, the solvent was evaporated and the residue was chormatographed on a column of silica gel to give 4n 90 mg (0.215 mmol, 81%).

Synthesis of 4O: To a solution of 3b 80 mg (0.210 mmol) in 5 ml of dichloromethane, 300 mg of trifluoroacetic anhydride was added. The solution was stirred for half an hour and then the solvent was evaporated under reduced pressure to give 4o, 100 mg (0.210 mmol, 100%).

Synthesis of 4p: A solution of 3g 100 mg (0.255 mmol), acetyl chloride 50 mg (0.64 mmol) and triethylamine 1300 mg (1.28 mmol), in 10 ml THF was stirred at 25° C. for 24 hours. Afterwards 50 ml of ether was added and the solution was washed with water three times. After it was dried over Na$_2$SO$_4$, the solvent was evaporated and the residue was chormatographed on a column of silica gel to give 4p 90 mg (0.19 mmol, 70%).

Synthesis of 4q: To a solution of 3h 100 mg (0.24 mmol) in 5 ml of dichloromethane, 300 mg of trifluoroacetic anhydride was added. The solution was stirred for half an hour and then the solvent was evaporated under reduced pressure to give 4q 120 mg (0.24 mmol, 100%).

Synthesis of 4r: To a solution of 3i 50 mg (0.124 mmol) in 5 ml of dichloromethane, 200 mg of trifluoroacetic anhydride was added. The solution was stirred for half an hour and then the solvent was evaporated under reduced pressure to give 4r 57 mg (0.124 mmol, 100%).

Synthesis of 4s: To a solution of 3j 50 mg in 5 ml of dichloromethane, 200 mg of trifluoroacetic anhydride was added. The solution was stirred for half an hour and then the solvent was evaporated under reduced pressure to give 4s 66 mg. Yield: 100%.

Synthesis of 4t: To a solution of 3d 50 mg in 5 ml of dichloromethane, 200 mg of trifluoroacetic anhydride was added. The solution was stirred for half an hour and then the solvent was evaporated under reduced pressure to give 4s 65 mg. Yield: 100%.

Synthesis of 4u: To a solution of 3n 50 mg in 5 ml of dichloromethane, 200 mg of trifluoroacetic anhydride was added. The solution was stirred for half an hour and then the solvent was evaporated under reduced pressure to give 4s 62 mg Yield: 100%.

The dithiolopyrroline derivatives prepared by using these intermediates above are listed in Table 5.

TABLE 5

Dithiolopyrrolone derivatives of formula I.

| Code | $R_1$ | $R_2$ | $R_3$ |
|---|---|---|---|
| 0003 | 4-Methoxyphenyl | H | Methyl |
| 0004 | 4-Methoxyphenyl | Acetyl | Methyl |
| 0005 | 4-Methoxyphenyl | H | Trifluoromethyl |
| 0007 | 2,4-Dimethoxy-phenyl | H | $CH_2CH_2COOH$ |
| 0008 | 4-Methylphenyl | H | Methyl |
| 0012 | 4-Methoxyphenyl | Benzyl | Trifluoromethyl |
| 0013 | 4-Hydroxyphenyl | Benzyl | Trifluoromethyl |
| 0014 | 2,4-Dimethoxy-phenyl | H | Methyl |
| 0017 | 3,4,5-trimethoxy-phenyl | H | Methyl |
| 0018 | 2,4-Dimethoxy-phenyl | H | 3-pyridyl |
| 0019 | 2,4-Dimethoxy-phenyl | H | N-methyl-3-pyridinium chloride |
| 0020 | 2,4-Dimethoxy-phenyl | H | Trifluoromethyl |
| 0022 | 1-ethylpyrazole-5-yl | H | Trifluoromethyl |
| 0030 | 2,4-Dimethoxy-phenyl | H | Hydroxymethyl |
| 0039 | 2,4-Dihydroxyphenyl | H | methyl |
| CSL-25 | Phenyl | H | Methyl |
| CSL-26 | Benzyl | H | Phenyl |
| CSL-28 | H | H | 3-pyridyl |

Therein A = C, B = O, n = 1.

Synthesis of 0003: A solution of 4p 90 mg (0.19 mmol) and Hg(OAc)$_2$ 6.8 mg (0.19 mmol) in 10 ml TFA was stirred at room temperature for one hour. After TFA was evaporated under reduced pressure, the residue was dissolved in 100 ml CH$_3$CN. H$_2$S was bubbled into the solution. One hour later, N$_2$ was bubbled into the solution to drive away trace of H$_2$S, then 0.20 mmol I$_2$ in 10 ml CH$_2$Cl$_2$ was added to the solution. Half an hour later, the solvent was evaporated under reduced pressure and the residue was chromatographed in a column of silica gel to give 0003 43 mg. Yield 67%. $^1$H NMR (100 MHz, CDCl$_3$) δ2.2(s, 3H), 3.9 (s, 3H), 6.7 (s, 1H), 7.0-7.4 (dd, 4H), 7.8 (s, 1H).

Synthesis of 0004: 0004 was synthesized from 4i by the same method of synthesis as 0003. Yield 60%. $^1$H NMR (100 MHz, CDCl$_3$) δ2.5 (s, 6H), 3.9 (s, 3H), 6.95 (s, 1H), 7.0-7.5 (dd, 4H), MS (CI): 363 (M+1).

Synthesis of 0005: 0005 was synthesized from 4j by the same method of synthesis as 0003. Yield 75%. $^1$H NMR (100 MHz, CDCl$_3$) δ3.9 (s, 3H), 6.82 (s, 1H), 7.0-7.4 (dd, 4H), 8.3 (s, 1H).

Synthesis of 0008: 0008 was synthesized from 4n by the same method of synthesis as 0003. yield: 70% $^1$H NMR (100 MHz, CDCl$_3$) δ2.1 (s, 3H), 2.4 (s, 3H), 6.7 (s, 1H), 7.3 (s, 4H), 8.0 (s, 1H).

Synthesis of 0012: 0012 was synthesized from 4k by the same method of synthesis as 0003. Yield: 72%. $^1$H NMR (100 MHz, CDCl$_3$) δ3.9 (s, 3H), 4.2-5.8 (dd, 2H), 6.9 (s, 1H), 7.0-7.4 (dd, 4H), 7.4 (s, 5H). MS (CI): 465 (M+1).

Synthesis of 0013: 0013 was synthesized from 4l by the same method of synthesis as 0003. Yield: 65%. $^1$H NMR (100 MHz, CDCl$_3$) δ4.2-5.8 (dd, 2H), 6.6 (s, 1H), 7.1-7.5 (broad peak, 9H), 7.4 (s, 5H).

Synthesis of 0014: 0014 was synthesized from 4 by the same method of synthesis as 0003. Yield: 77%. $^1$H NMR (100 MHz, CDCl$_3$) δ2.73 (s, 3H), 3.77 (s, 3H), 3.82 (s, 3H), 6.6 (s, 1H), 6.4-7.3 (multi, 3H), 8.0 (broad peak, 1H). MS: 350 (M).

Synthesis of 0017: 0017 was synthesized from 4m by the same method of synthesis as 0003. Yield: 55%. $^1$H NMR (100 MHz, CDCl$_3$) δ3.8 (s, 6H), 3.9 (s, 3H), 6.7 (s, 1H), 7.4 (s, 2H), 7.9 (broad peak, 1H). MS: 380 (M).

Synthesis of 0018: 0018 was synthesized from 4b by the same method of synthesis as 0003. Yield: 45%. $^1$H NMR (100 MHz, CD$_3$OD) δ3.8 (s, 3H), 3.9 (s, 3H), 6.7 (s, 1H), 6.6-9.2 (multi, 7H).

Synthesis of 0019: 10 mg (0.024 mmol) 0018 was dissolved in 1 ml CH$_3$I and the solution left at room temperature for 10 hours. Red crystals formed in the solution which was filtered and 9 mg (0.016 mmol) 0019 was obtained in 67%. $^1$H NMR (100 MHz, CD$_3$OD) δ3.7 (s, 3H), 3.8 (s, 3H), 4.4 (s, 3H), 6.9 (s, 1H), 6.5-9.4 (multi, 7H).

Synthesis of 0020: 0020 was synthesized from 4c by the same method of synthesis as 0003. Yield: 83%. $^1$H NMR (100 MHz, CDCl$_3$) δ3.8 (s, 3H), 3.9 (s, 3H), 6.6 (multi, 3H), 7.2 (d, 1H), 8.4 (s, 1H). MS: CI 405 (M+1).

Synthesis of 0022: 0022 was synthesized from 4o by the same method of synthesis as 0003. Yield: 6.6%. $^1$H NMR (100 MHz, CDCl$_3$) δ1.5 (t, 3H), 4.0 (q, 2H), 6.3 (d, 1H), 6.9 (s, 1H), 7.7 (d, 1H), 8.4 (s, 1H). MS: CI 363 (M+1).

Synthesis of 0024: 0024 was synthesized from 4d by the same method of synthesis as 0003.19%. $^1$H NMR (100 MHz, CDCl$_3$) δ2.6 (s, 6H), 3.8 (s, 3H), 3.9 (s, 3H), 6.4 (s, 1H), 6.5 (multi, 2H), 7.2 (d, 1H). MS: 337 (M+1).

Synthesis of 0028: 0028 was synthesized from 4f by the same method of synthesis as 0003. Yield: 43%. $^1$H NMR (100 MHz, CDCl$_3$), δ3.8 (s, 3H), 3.9 (s, 3H), 6.5 (s, 1H), 6.65 (multi, 4H), 7.2 (multi, 2H), 7.7 (multi, 3H). MS: 529 (M+1).

Synthesis of 0030: 0030 was synthesized from 4g by the same method of synthesis as 0003. Yield: 41%. $^1$H NMR (100 MHz, CDCl$_3$), δ3.8 (s, 3H), 3.9 (s, 3H), 4.3 (s, 2H), 6.5 (s, 1H), 6.65 (multi, 2H), 7.2 (d, 1H), 8.35 (s, 1H). MS: 367 (M+1).

Synthesis of CSL-25: CSL-25 was synthesized using the procedure of Scheme 1. CSL-25 has the following characteristics: $^1$H NMR (100 MHz, CDCl$_3$) δ2.2 (s, 3H), 6.8 (s, 1H), 7.4-7.6 (multi, 5H), 7.8 (s, 1H).

Synthesis of CSL-26: CSL-26 was synthesized using the procedure of Scheme 1. CSL-26 has the following characteristics: $^1$H NMR (100 MHz, CDCl$_3$) δ5.1 (s, 2H), 6.5 (s, 1H), 7.2-8.0 (multi, 10H), 8.3 (s, 1H).

Synthesis of CSL-28: CSL-28 was synthesized from 4h by the same method of synthesis as 0003. Yield: 43%. $^1$H NMR (100 MHz, CDCl$_3$), δ 6.8 (s, 1H), 7.9 (s, 1H), 8.1-9.2 (multi 4H), MS: CI, 278 (M+1).

Synthesis of 0050: 0050 was synthesized from 4q by the same method of synthesis as 0003. Yield: 80%. $^1$H NMR (100 MHz, CDCl$_3$), δ0.9 (t, 3H), 1.3 (d, 3H), 1.65 (multi, 2H), 2.7 (multi, 1H), 6.9 (s, 1H), 7.3 (s, 4H), 8.4 (s, 1H).

Synthesis of 0061: 0061 was synthesized from 4s by the same method of synthesis as 0003. Yield: 82%. $^1$H NMR (100 MHz, CDCl$_3$), 2.8 (s, 3H), 6.6 (s, 1H), 8.4 (s, 1H).

Synthesis of 0092: 0092 was synthesized from 4r by the same method of synthesis as 0003. Yield: 77%. $^1$H NMR (100 MHz, CDCl$_3$), δ1.26 (d, 6H), 3.0 (multi, 1H), 6.7 (s, 1H), 7.35 (s, 4H), 8.6 (s, 1H).

Synthesis of 0103: 0103 was synthesized from 4t by the same method of synthesis as 0003. Yield: 85%. $^1$H NMR (100 MHz, CDCl$_3$), 4.3 (s, 2H), 6.6 (s, 1H), 7.3 (s, 5H), 8.4 (s, 1H).

Synthesis of 0119: 0119 was synthesized from 4u by the same method of synthesis as 0003. Yield: 85%. $^1$H NMR (100 MHz, CDCl$_3$), 62.7 (s, 3H), 3.8 (s, 3H), 3.85 (s, 3H), 6.55 (s, 1H), 6.6 (multi, 2H), 7.2 (d, 1H), 8.4 (s, 1H).

The following synthesis route (Scheme 2) is effective way to synthesize analogues when R$_3$ is group of —NR$_4$R$_5$, —OR$_6$ and —NHSO$_2$R$_6$, aryl, heterocyclic or some groups which are unstable under the reaction conditions of the last step in Scheme 1.

The following compounds are prepared according to the following synthetic scheme (Scheme 2):

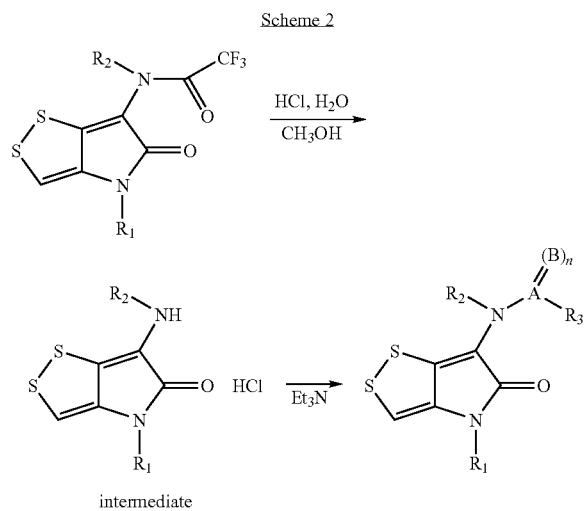

intermediate

By the method described in Scheme 2, some intermediates are synthesized and listed in table 6.

TABLE 6 intermediates for the synthesis of dithiolopyrrolone derivatives

| Code | R$_1$ | R$_2$ |
|---|---|---|
| 0021 | 2,4-dimethoxyphenyl | H |
| 0051 | 4-isobutylphenyl | H |
| 0079 | Methyl | H |
| 0093 | 4-isopropanylphenyl | H |
| 0104 | Benzyl | H |
| 0120 | 2,4-dimethoxyphenyl | Methyl |

Synthesis of 0021: 0020 (1 g) was dissolved in a solution of 5 ml hydrochloric acid in 150 ml methanol. The solution was refluxed for 2 hours. After the solvent was evaporated in vacuum, 0021 (0.76 g) was collected as a dark green powder.

Intermediates 0051, 0079, 0093, 0104, and 0120 were synthesized by the same method as used in the synthesis of 0021 from the start materials of 0050, 0061, 0092, 0103 and 0119 respectively.

The dithiolopyrrolone derivatives prepared by method described in Scheme 2 are listed in Table 7.

TABLE 7

Dithiolopyrrolone derivatives of formula I.

| Code | R$_1$ | R$_2$ | R$_3$ |
|---|---|---|---|
| 0023 | 2,4-Dimethoxy-phenyl | H | 2-furyl |
| 0025 | 2,4-Dimethoxy-phenyl | H | 2,4-dimethoxyphenyl |
| 0026 | 2,4-Dimethoxy-phenyl | H | 4-Trifluoromethylphenyl |
| 0029 | 2,4-Dimethoxy-phenyl | H | 2-thiophenyl |
| 0032 | 2,4-Dimethoxy-phenyl | H | 3,5-difluorophenyl |
| 0033 | 2,4-Dimethoxy-phenyl | H | 2,3,4-trifluorophenyl |
| 0036 | 2,4-Dimethoxy-phenyl | H | 4-fluoro-phenyl |
| 0037 | 2,4-Dimethoxy-phenyl | H | Thiophene-2-methyl |
| 0038 | 2,4-Dimethoxy-phenyl | H | 4-nitrophenyl |
| 0040 | 2,4-Dimethoxy-phenyl | H | 4-N,N-dimethylamine-phenyl |
| 0041 | 2,4-Dimethoxy-phenyl | H | 4-aminophenyl |
| 0042 | 2,4-Dimethoxy-phenyl | H | 2,2,5,5-Tetramethyl-tetrahydro-1,3,4,6,8-pentaoxa-cyclopenta[a]inden-8a-yl |
| 0043 | 2,4-Dimethoxy-phenyl | H | 6-Hydroxy-5-hydroxymethyl-2,2-dimethyl-dihydro-furo[2,3-d][1,3]dioxol-3a-yl |
| 0044 | 2,4-Dimethoxy-phenyl | H | 2,3,4-Trihydroxy-5-hydroxymethyl-tetrahydro-furan-2-yl |
| 0047 | 2,4-Dimethoxy-phenyl | H | 3-trifluoromethylphenyl |
| 0052 | 2,4-Dimethoxy-phenyl | H | 4-Morpholin-4-ylmethyl |
| 0046 | 2,4-Dimethoxy-phenyl | H | 1,2,3,4,5-Pentahydroxy-pentyl |
| 0054 | 4-iso-butylphenyl | H | 4-trifluoromethylphenyl |
| 0055 | 4-iso-butylphenyl | H | 2-furyl |
| 0056 | 4-iso-butylphenyl | H | 2-thiophenyl |
| 0057 | 4-iso-butylphenyl | H | 3-trifluoromethylphenyl |
| 0058 | 2,4-Dimethoxy-phenyl | H | 3,5-di-trifluoromethylphenyl |
| 0059 | 4-iso-butylphenyl | H | 3,5-di-trifluoromethylphenyl |
| 0062 | 2,4-Dimethoxy-phenyl | H | 4-Piperazin-1-ylmethyl |
| 0066 | 2,4-Dimethoxy-phenyl | H | 4-Morpholin-4-ylmethyl-phenyl |
| 0068 | 2,4-Dimethoxy-phenyl | H | 4-(4-Methyl-piperazin-1-ylmethyl)-phenyl |
| 0069 | 2,4-Dimethoxy-phenyl | H | 4-Piperazin-1-ylmethyl-phenyl |

TABLE 7-continued

Dithiolopyrrolone derivatives of formula I.

| Code | R$_1$ | R$_2$ | R$_3$ |
| --- | --- | --- | --- |
| 0185 | 4-isopropylphenyl | H | 4-(4-Methyl-piperazin-1-ylmethyl)-phenyl |
| 0187 | 4-isobutylphenyl | H | 4-(4-Methyl-piperazin-1-ylmethyl)-phenyl |
| 0189 | methyl | H | 4-(4-Methyl-piperazin-1-ylmethyl)-phenyl |
| 0096 | 4-isopropanylphenyl | H | 3,5-dihydroxy-4-isopropanyl-phenyl |
| 0102 | 2,4-Dimethoxy-phenyl | H | 3,5-dihydroxy-4-isopropanyl-phenyl |
| 0107 | Benzyl | H | 3,5-dihydroxy-4-isopropanyl-phenyl |
| 0110 | methyl | H | 3,5-dihydroxy-4-isopropanyl-phenyl |
| 0113 | Benzyl | H | 2-thiophenyl |
| 0116 | Benzyl | H | 4-Morpholin-4-ylmethyl-phenyl |
| 0122 | 2,4-Dimethoxy-phenyl | methyl | 4-Morpholin-4-ylmethyl-phenyl |
| 0125 | 4-isopropanylphenyl | H | 3-Morpholin-4-ylmethyl-phenyl |
| 0126 | 2,4-Dimethoxy-phenyl | H | 3-Morpholin-4-ylmethyl-phenyl |
| 0128 | 4-isopropanylphenyl | H | Pyridine-3-yl |
| 0135 | Benzyl | H | Pyridine-3-yl |
| 0136 | Benzyl | H | 3-(4-Methyl-piperazin-1-ylmethyl)-phenyl |
| 0137 | Benzyl | H | 3-Morpholin-4-ylmethyl-phenyl |
| 0211 | 2,4-Dimethoxy-phenyl | H | 3,5-Bis-trifluoromethyl-phenylamino |
| 0212 | 2,4-Dimethoxy-phenyl | H | Toluene-4-sulfonylamino |
| 0213 | 2,4-Dimethoxy-phenyl | H | 2,4-Difluoro-phenylamino |
| 0227 | 2,4-Dimethoxy-phenyl | H | phenoxy |
| 0228 | 2,4-Dimethoxy-phenyl | H | 2-methylpropoxy |
| 0229 | 2,4-Dimethoxy-phenyl | H | benzoxy |
| 0230 | 2,4-Dimethoxy-phenyl | H | ethoxy |
| 0231 | 2,4-Dimethoxy-phenyl | H | methoxy |
| 0232 | 2,4-Dimethoxy-phenyl | H | H |
| 0233 | 2,4-Dimethoxy-phenyl | H | isopropoxy |
| 0234 | 2,4-Dimethoxy-phenyl | H | propynoxy |
| 0235 | 2,4-Dimethoxy-phenyl | H | propoxy |
| 0236 | 2,4-Dimethoxy-phenyl | H | 4-methoxyphenoxy |
| 0237 | 2,4-Dimethoxy-phenyl | H | n-pentanoxy |
| 0238 | 2,4-Dimethoxy-phenyl | H | pyranylmethoxy |
| 0239 | 2,4-Dimethoxy-phenyl | H | n-butoxy |
| 0240 | 2,4-Dimethoxy-phenyl | H | cyclopentanoxy |
| 0241 | 2,4-Dimethoxy-phenyl | H | n-heptoxy |
| 0242 | 2,4-Dimethoxy-phenyl | H | 2-Chloro-phenoxy |
| 0243 | 2,4-Dimethoxy-phenyl | H | 4-Chloro-phenoxy |
| 0244 | 2,4-Dimethoxy-phenyl | H | 4-p-Tolyloxy |
| 0245 | 2,4-Dimethoxy-phenyl | H | 2-furylmethoxy |
| 0246 | 2,4-Dimethoxy-phenyl | H | 1-phenylethoxy |
| 0247 | 2,4-Dimethoxy-phenyl | H | 2-thienylmethoxy |
| 0248 | 2,4-Dimethoxy-phenyl | H | Pyridin-3-yloxy |
| 0249 | 2,4-Dimethoxy-phenyl | H | Bis-(2-hydroxy-ethyl)-amino |
| 0250 | 2,4-Dimethoxy-phenyl | H | benzylamino |
| 0251 | 2,4-Dimethoxy-phenyl | H | butylamino |
| 0252 | 2,4-Dimethoxy-phenyl | H | Phenylamino |
| 0253 | 2,4-Dimethoxy-phenyl | H | Ethylsulfanyl |
| 0254 | 2,4-Dimethoxy-phenyl | H | ethoxy |
| 0255 | 2,4-Dimethoxy-phenyl | H | penoxy |
| 0256 | 2,4-Dimethoxy-phenyl | H | propynoxy |
| 0257 | 2,4-Dimethoxy-phenyl | H | N,N-dimethylaminoethoxy |
| 0258 | 2,4-Dimethoxy-phenyl | H | N-methylaminoethoxy |
| 0259 | 2,4-Dimethoxy-phenyl | H | N,N-dimethylaminoethoxy | wherein A = C, B = O, n = 1.

TABLE 8

Dithiolopyrrolone derivatives of formula I.

| Code | R$_1$ | R$_2$ | R$_3$ |
| --- | --- | --- | --- |
| 0214 | 2,4-Dimethoxy-phenyl | H | 3,5-Difluoro-phenylamino |
| 0215 | 2,4-Dimethoxy-phenyl | H | methyl |

When A = C, B = S, n = 1, compound is 0214. When A = S, B = O and n = 2, the compound is 0215.

Synthesis of 0023: 50 mg (0.16 mmol) 0021 was dissolved in 20 ml dry THF. While thoroughly stirring, 43 mg (0.32 mmol) 2-furoyl chloride was added first then 50 mg triethylamine was added dropwise over 2 minutes. The reaction was completed in half an hour and the product was purified by a column of silica gel to give 51 mg (0.12 mmol, 80%) 0023. $^1$H NMR (100 MHz, CDCl$_3$) δ3.8 (s, 3H), 3.9 (s, 3H), 6.5 (s, 1H), 6.6 (s multi, 3H), 7.2 (multi, 2H), 7.6 (d, 1H), 8.4 (s, 1H). MS: 403 (M+1).

Synthesis of 0025: 0025 was synthesized by the reaction of 0021 with 2,4-dimethoxy benzoyl chloride by the same method of synthesis as 0023. Yield: 89%. $^1$H NMR (100 MHz, CDCl$_3$) δ3.8 (s, 3H), 3.9 (s, 3H), 3.93 (s, 3H), 4.07 (s, 3H), 6.4 (s, 1H), 6.6 (multi, 4H), 7.2 (d, 1H), 8.2 (d, 1H), 10.2 (s, 1H). MS: 473 (M+1).

Synthesis of 0026: 0026 was synthesized by the reaction of 0021 with 4-trifluoromethyl benzoyl chloride by the same method of synthesis as 0023. Yield: 90%. $^1$H NMR (100 MHz, CDCl$_3$) δ3.8 (s, 3H), 3.9 (s, 3H), 6.5 (s, 1H), 6.6 (multi, 2H), 7.25 (d, 1H), 7.8 (d, 2H), 8.1 (d, 2H), 8.4 (s, 1H). MS: 480 (M).

Synthesis of 0029: 0029 was synthesized by the reaction of 0021 with 2-thiophenecarbonyl chloride by the same method of synthesis as 0023. Yield: 88%. $^1$H NMR (100 MHz, CDCl$_3$), 63.8 (s, 3H), 3.9 (s, 3H), 6.55 (s, 1H), 6.63 (multi, 2H), 7.2 (multi, 2H), 7.7 (multi, 2H). MS: 418 (M).

Synthesis of 0031: 0031 was synthesized by the reaction of 0021 with heptanoyl chloride by the same method of synthesis as 0023. Yield: 74%. $^1$H NMR (100 MHz, CDCl$_3$), 60.9 (t, 3H), 1.4 (multi, 8H), 2.4 (t, 2H), 3.8 (s, 3H), 3.9 (s, 3H), 4.3 (s, 2H), 6.6 (s, 1H), 6.65 (multi, 2H), 7.2 (d, 1H), 8.4 (s, 1H). MS: 420 (M).

Synthesis of 0032: 0032 was synthesized by the reaction of 0021 with 3,4-difluorobenzoyl chloride by the same method of synthesis as 0023. Yield: 81%. $^1$H NMR (100 MHz, CDCl$_3$), 63.8 (s, 3H), 3.9 (s, 3H), 6.5 (s, 1H), 6.6 (multi, 2H), 7.1 (multi, 2H), 7.5 (multi, 2H), 8.4 (s, 1H). MS: 448 (M).

Synthesis of 0033: 0033 was synthesized by the reaction of 0021 with 2,3,4-trifluorobenzoyl chloride by the same method of synthesis as 0023. Yield: 84%. $^1$H NMR (100 MHz, CDCl$_3$), 63.8 (s, 3H), 3.9 (s, 3H), 6.5 (s, 1H), 6.6 (multi, 2H), 7.2 (multi, 2H), 7.9 (multi, 1H), 8.6 (s, 1H). MS: 466 (M).

Synthesis of 0036: 0036 was synthesized by the reaction of 0021 with 4-fluorobenzoyl chloride by the same method of synthesis as 0023. Yield: 85%. $^1$H NMR (100 MHz, CDCl$_3$), 63.8 (s, 3H), 3.9 (s, 3H), 6.5 (s, 1H), 6.65 (multi, 3H), 7.1 (multi, 2H), 7.5 (multi, 2H), 8.4 (s, 1H). MS: 430 (M).

Synthesis of 0037: 0037 was synthesized by the reaction of 0021 with thiopheneacetyl chloride by the same method of synthesis as 0023. Yield: 81%. $^1$H NMR (100 MHz, CDCl$_3$), 63.75 (s, 3H), 3.85 (s, 3H), 3.9 (s, 2H), 6.42 (s, 1H), 6.55 (multi, 2H), 7.1-7.3 (multi, 4H), 8.2 (s, 1H). MS: 433 (M+1).

Synthesis of 0038.: 0038 was synthesized by the reaction of 0021 with 4-nitrobenzoyl chloride by the same method of synthesis as 0023. Yield: 81%. $^1$H NMR (100 MHz, CDCl$_3$), 63.8 (s, 3H), 3.85 (s, 3H), 6.55 (multi, 2H), 7.1-7.3 (dd, 1H), 8.2 (dd, 4H), 8.9 (s, 1H). MS: 458 (M+1).

Synthesis of 0040: 100 mg (0.32 mmol), 0021 55 mg (0.32 mmol) 4-(dimethylamino)benzoic acid and 75 mg (0.34 mmol) DCC were dissolved in 20 ml dry CH$_2$Cl$_2$. This solution had been stirred for 2 hours. After the solvent was evaporated, product was purified by a column of silica gel to give 65 mg(60%) 0040. $^1$H NMR (100 MHz, CDCl$_3$), 63.1 (s, 6H), 3.8 (s, 3H), 3.85 (s, 3H), 6.4 (s, 1H), 6.5 (multi, 2H), 6.8 (d, 2H), 7.25 (d, 1H), 7.85 (d, 2H), 8.1 (s, 1H). MS: 456 (M+1).

Synthesis of 0041: 100 mg (0.32 mmol), 0021 80 mg (0.32 mmol) 4-trifloroacetamidobenzoic acid and 75 mg (0.34 mmol) DCC were dissolved in 20 ml dry CH$_2$Cl$_2$. This solution had been stirred for 2 hours. After the solvent was evaporated, residue was dissolved in 40 ml methanol. To this solution 2 ml concentrated HCl was added and the resulting solution was refluxed for 1 hour. Product was extracted with ethyl acetate and washed with water dried on sodium sulfate. After solvent was evaporated the residue was chromatographed on a column of silica gel to give 50 mg (40%) 0041. $^1$H NMR (100 MHz, DMSO-d$_6$), 63.7 (s, 3H), 3.8 (s, 3H), 5.9 (s, 2H), 6.6 (d, 2H), 6.7 (multi, 2H), 6.8 (s, 1H), 7.2 (d, 1H), 7.75 (d, 2H), 9.55 (s, 1H). MS: 428 (M+1).

Synthesis of 0042: 100 mg (0.32 mmol), 0021, 100 mg (0.33 mmol) 2,3:4,6-di-O-isopropylidene-2-keto-L-gulonic acid monohydrate and 80 mg (0.35 mmol) DCC were dissolved in 20 ml dry CH$_2$Cl$_2$. This solution had been stirred for 2 hours. After the solvent was evaporated, residue was chromatographed on a column of silica gel to give 110 mg(60%) 0042. $^1$H NMR (100 MHz, CDCl$_3$), 61.4 (s, 3H), 1.42 (s, 3H), 1.6 (s, 6H), 3.75 (s, 3H), 3.85 (s, 3H), 4.1-4.7 (multi, 5H), 6.4 (s, 1H), 6.5-6.6 (multi, 2H), 7.2 (d, 1H), 9.0 (s, 1H). MS: 565 (M+1).

Synthesis of 0043: A solution of 50 mg 0042 in 20 ml mixture of 1N HCl and THF (1:5) was stirred at room temperature for 3 hours. Product was extracted with ethyl acetate and washed with water. After solvent was evaporated, residue was chromatographed on a column of silica gel to give 42 mg (85%) 0043. $^1$H NMR (100 MHz, CDCl$_3$), 61.4 (s, 3H), 1.42 (s, 3H), 3.8 (s, 3H), 3.9 (s, 3H), 4.1-4.7 (multi, 5H), 6.5 (s, 1H), 6.5-6.6 (multi, 2H), 7.2 (d, 1H), 9.0 (s, 1H). MS: 525 (M+1).

Synthesis of 0044: A solution of 50 mg 0042 in 20 ml mixture of acetic acid and water (7:3) was refluxed for 4 hours. Solvents were evaporated under reduced pressure. Residue was chromatographed on a column of silica gel to give 36 mg(85%) 0044. $^1$H NMR (100 MHz, CDCl$_3$), 62.6-4.5 (broad, 10H), 3.8 (s, 3H), 3.9 (s, 3H), 6.5-6.6 (multi, 3H), 7.2 (d, 1H), 9.0 (s, 1H). MS: 485 (M+1).

Synthesis of 0047: The synthesis of 0047 was achieved by the reaction of 0021 with 3-trifluoromethylbenzoyl chloride by the same method of synthesis as 0023. Yield: 85%. $^1$H NMR (100 MHz, CDCl$_3$), 63.8 (s, 3H), 3.85 (s, 3H), 6.55 (s, 1H), 6.6 (multi, 2H), 7.2 (d, 1H), 7.8 (s, 1H), 7.7-8.4 (multi, 4H). MS: 487 (M+1).

Synthesis of 0052: 100 mg 0021 was dissolved in 40 ml dry THF. While stirring thoroughly, 100 mg chloroacetyl chloride was added then 50 mg triethylamine was added dropwise over 2 minutes. The reaction was completed in half an hour. Product was extracted with ethyl acetate and washed with water. After the solvent was evaporated the residue was dissolved in 10 ml of acetonitrile. To this solution, 0.5 ml of morpholine was added and the solution was stirred at 60° C. for 4 hours. Product was extracted with ethyl acetate and washed with water. After solvent was evaporated, residue was chromatographed on a column of silica gel to give 0052 65 mg Yield: 50%. $^1$H NMR (100 MHz, CDCl$_3$), 62.8 (multi, 4H), 3.8 (multi, 4H), 3.81 (s, 3H), 3.85 (s<3H), 6.45 (s, 1H), 6.6 (multi, 2H), 7.25 (d, 1H), 9.45 (s, 1H). MS: 436 (M+1).

Synthesis of 0054: The compound 0054 was synthesized by the reaction of 0051 and 4-trifloromethyl benzoyl chloride using the same method of synthesis as for 0023. Yield: 85%. $^1$H NMR (100 MHz, CDCl$_3$), 60.9 (t, 3H), 1.3 (d, 3H), 1.65 (multi, 2H), 2.7 (multi, 1H), 6.9 (s, 1H), 7.3 (s, 4H), 7.8 (d, 2H), 8.1 (d, 2H), 8.4 (s, 1H). MS: 477 (M+1).

Synthesis of 0055: The compound 0055 was synthesized by the reaction of 0051 and 2-furoyl chloride using the same method of synthesis as for 0023. Yield: 90%. $^1$H NMR (100 MHz, CDCl$_3$), 60.9 (t, 3H), 1.3 (d, 3H), 1.65 (multi, 2H), 2.7 (multi, 1H), 6.6 (dd, 1H), 6.9 (s, 1H), 7.3 (s, 4H), 7.4 (d, 1H), 7.6 (d, 1H), 8.4 (s, 1H). MS: 413 (M+1).

Synthesis of 0056: The compound 0056 was synthesized by the reaction of 0051 and 2-thiophenecarbonyl chloride using the same method of synthesis as for 0023. Yield: 90%. $^1$H NMR (100 MHz, CDCl$_3$), 60.9 (t, 3H), 1.3 (d, 3H), 1.65 (multi, 2H), 2.7 (multi, 1H), 6.85 (s, 1H), 7.2 (dd, 1H), 7.3 (s, 4H), 7.6 (d, 2H), 7.8 (d, 2H), 8.2 (s, 1H). MS: 429 (M+1).

Synthesis of 0057: The compound 0057 was synthesized by the reaction of 0051 and 3-trifloromethyl benzoyl chloride using the same method of synthesis as for 0023. Yield: 88%. $^1$H NMR (100 MHz, CDCl$_3$), 60.9 (t, 3H), 1.3 (d, 3H), 1.65 (multi, 2H), 2.7 (multi, 1H), 6.9 (s, 1H), 7.35 (s, 4H), 7.6-8.3 (multi, 4H), 8.4 (s, 1H). MS: 477 (M+1).

Synthesis of 0058:(N-[4-(2,4-Dimethoxy-phenyl)-5-oxo-4,5-dihydro-[1,2]dithiolo[4,3-b]pyrrol-6-yl]-3,5-bis-trifluoromethyl-benzamide). The compound 0058 was synthesized by the reaction of 0021 and 3,5-di-trifloromethyl benzoyl chloride using the same method of synthesis as for 0023. Yield: 88%. $^1$H NMR (100 MHz, CDCl$_3$), 63.8 (s, 3H), 3.85

(s, 3H), 6.55 (s, 1H), 6.6 (multi, 2H), 7.2 (d, 1H), 8.1 (s, 1H), 8.4 (s, 2H), 8.6 (s, 1H). MS: 545 (M+1).

Synthesis of 0059: The compound 0059 was synthesized by the reaction of 0051 and 3,5-di-trifloromethyl benzoyl chloride using the same method of synthesis as for 0023. Yield: 80%. $^1$H NMR (100 MHz, CDCl$_3$), 60.9 (t, 3H), 1.3 (d, 3H), 1.65 (multi, 2H), 2.7 (multi, 1H), 6.95 (s, 1H), 7.3 (s, 4H), 8.1 (s, 1H), 8.4 (s, 2H), 8.6 (s, 1H). MS: 549 (M+1).

Synthesis of 0062: 100 mg 0021 was dissolved in 40 ml dry THF. While stirring thoroughly, 100 mg chloroacetyl chloride was added, then 100 mg triethylamine was added dropwise over 2 minutes. The reaction was completed in half an hour. Product was extracted with ethyl acetate and washed with water. After the solvent was evaporated the residue was dissolved in 10 ml of DMF. To this solution, 200 mg of piperazine was added and the solution was stirred at 60° C. for 4 hours. Product was extracted with ethyl acetate and washed with water. After solvent was evaporated, the residue was chromatographed on a column of silica gel to give 0062 70 mg Yield: 53%. $^1$H NMR (100 MHz, CDCl$_3$), 62.7 (multi, 4H), 3.1 (multi, 4H), 3.2 (s, 2H), 3.4 (s, 1H), 3.8 (s, 3H), 3.9 (s, 3H), 6.4 (s, 1H), 6.6 (multi, 2H), 7.2 (d, 1H), 9.2 (s, 1H). MS: 435 (M+1).

Synthesis of 0066: 100 mg 0021 was dissolved in 40 ml dry THF. While stirring thoroughly, 120 mg 4-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of morpholine. This solution was stirred at 60° C. for 2 hours and water was added. Product was extracted with ethyl acetate and washed with water. After solvent was evaporated, the residue was chromatographed on a column of silica gel to give 0066 110 mg. Yield: 68%. $^1$H NMR (100 MHz, CDCl$_3$), 62.5 (multi, 4H), 3.8 (multi, 4H), 3.6 (s, 2H), 3.85 (s, 3H), 3.9 (s, 3H), 6.5 (s, 1H), 6.6 (multi, 2H), 7.2 (d, 1H), 7.7 (dd, 4H), 8.3 (s, 1H). MS: 512 (M+1).

Synthesis of 0068: 100 mg 0021 was dissolved in 40 ml dry THF. While stirring thoroughly, 120 mg 4-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of N-methyl piperazine. This solution was stirred at 60° C. for 2 hours and water was added. Product was extracted with ethyl acetate and washed with water. After solvent was evaporated, the residue was chromatographed on a column of silica gel to give 0068 120 mg Yield: 70%. $^1$H NMR (100 MHz, CDCl$_3$), 62.4 (s, 3H), 2.6 (s, 8H), 3.6 (s, 2H), 3.85 (s, 3H), 3.9 (s, 3H), 6.45 (s, 1H), 6.6 (multi, 2H), 7.2 (d, 1H), 7.7 (dd, 4H), 8.3 (s, 1H). MS: 525 (M+1).

Synthesis of 0069: 100 mg 0021 was dissolved in 40 ml dry THF. While stirring thoroughly, 120 mg 4-chloromethyl benzonyl chloride was added, then 100 mg triethylamine was added dropwise over 2 minutes. The reaction was completed in half an hour. Product was extracted with ethyl acetate and washed with water. After the solvent was evaporated the residue was dissolved in 10 ml of DMF. To this solution, 200 mg of piperazine was added and the solution was stirred at 60° C. for 4 hours. Product was extracted with ethyl acetate and washed with water. After the solvent was evaporated, the residue was chromatographed on a column of silica gel to give 0069 125 mg Yield: 70%. $^1$H NMR (100 MHz, CDCl$_3$), 62.6 (s, 4H), 3.1 (multi, 4H), 3.6 (s, 2H), 3.85 (s, 3H), 3.9 (s, 3H), 6.5 (s, 1H), 6.6 (multi, 2H), 7.25 (d, 1H), 7.7 (dd, 4H), 8.4 (s, 1H). MS: 511 (M+1).

Synthesis of 0080: 80 mg 0079 was dissolved in 20 ml of dry THF. To this solution 150 mg of 3-nicotinoyl carbonyl chloride was added and 100 mg of triethylamine was added dropwise. The resulting solution was stirred at room temperature for half an hour. Product was extracted with ethyl acetate and washed with water. After solvent was evaporated, the residue was chromatographed on a column of silica gel to give 0080 90 mg. Yield 80%. $^1$H NMR (100 MHz, CD$_3$OD) δ2.8 (s, 3H), 6.7 (s, 1H), 7.6 (d, 1H), 8.4 (dd, 1H), 8.7 (s, 1H), 8.9 (d, 1H), 9.2 (s, 1H). MS: 292 (M+1).

Synthesis of 0110: 80 mg 0079 was dissolved in 20 ml of dry THF. To this solution 180 mg of 3,5-dimethoxyl-4-isopropyl benzoyl chloride was added and 100 mg of triethylamine was added dropwise while stirring. The resulting solution was stirred at room temperature for half an hour. Product was extracted with ethyl acetate and washed with water. After the solvent was evaporated, the residue was dissolved in 5 ml of dichloromethane and to this solution, 100 mg BBr$_3$ was added at −78° C. This solution was stirred overnight at room temperature, then 100 ml water was added and the product was extracted with ethyl acetate and dried on sodium sulfate. After solvent was evaporated, the residue was chromatographed on a column of silica gel to give 0110 50 mg. Yield 40%. $^1$H NMR (100 MHz, CDCl$_3$), 61.24 (d, 3H), 1.26 (d, 3H), 3.1 (multi, 1H), 2.75 (s, 3H), 6.6 (s, 1H), 6.95 (s, 2H), 8.3 (s, 1H). MS: 565 (M+1).

Synthesis of 0096: 100 mg 0093 was dissolved in 20 ml of dry THF. To this solution 180 mg of 3,5-dimethoxyl-4-isopropyl benzoyl chloride was added and 100 mg of triethylamine was added dropwise while stirring. The resulting solution was stirred at room temperature for half an hour. Product was extracted with ethyl acetate and washed with water. After solvent was evaporated, the residue was dissolved in 5 ml of dichloromethane and to this solution, 100 mg BBr$_3$ was added at −78° C. This solution was stirred overnight at room temperature, then 100 ml water was added and the product was extracted with ethyl acetate and dried on sodium sulfate. After solvent was evaporated, the residue was chromatographed on a column of silica gel to give 0096 60 mg. Yield: 43%. $^1$H NMR (100 MHz, CDCl$_3$), 61.24 (d, 6H), 1.26 (d, 6H), 3.05 (multi, 2H), 6.88 (s, 1H), 6.98 (s, 2H), 7.3 (s, 4H). MS: 469 (M+1).

Synthesis of 0102: 0021 100 mg, 3,5-diacetoxy-4-isopropyl benzoic acid 80 mg and DCC 80 mg were added in 10 ml dry dichloromethane. This solution was stirred for 2 hours at room temperature. After purification by column chromatographer, the product was dissolved in 20 ml methanol. To this solution, a solution of 50 mg sodium carbonate in 2 ml water was added and the resulting solution was stirred at 50° C. for 4 hour. Product was extracted with ethyl acetate and washed with water and purified by column to give 0102 30 mg. Yield: 16%.

$^1$H NMR (100 MHz, CDCl$_3$), 61.24 (d, 6H), 1.26 (d, 6H), 3.1 (multi, 1H), 3.75 (s, 3H), 3.85 (s, 3H), 6.6 (s, 1H), 6.62 (multi, 2H), 6.95 (s, 2H), 7.2 (d, 1H), 8.3 (s, 1H). MS: 487 (M+1).

Synthesis of 0107: The compound 0107 was synthesized from 0104 by the same method as the synthesis of 0096. Yield 52%. $^1$H NMR (100 MHz, CDCl$_3$), δ 1.25 (d, 3H), 1.27 (d, 3H), 3.05 (multi, 1H), 5.02 (s, 2H), 6.6 (s, 1H), 6.95 (s, 2H), 7.1 (s, 5H), 8.4 (s, 1H). MS: 441 (M+1).

Synthesis of 0113: The compound 0113 was synthesized by the reaction of 0104 and 2-thiophenecarbonyl chloride by the same method of synthesis as 0023. Yield: 90%. $^1$H NMR (100 MHz, CDCl$_3$), δ 5.05 (s, 2H), 6.85 (s, 1H), 7.2 (dd, 1H), 7.25 (s, 5H), 7.6 (d, 1H), 7.8 (d, 1H), 8.3 (s, 1H). MS: 373 (M+1).

Synthesis of 0116: The compound 0116 was synthesized from 0104 by the same method of synthesis as 0066. Yield: 50% $^1$H NMR (100 MHz, CDCl$_3$), 62.5 (multi, 4H), 3.6 (s, 2H), 3.8 (multi, 4H), 4.9 (s, 2H), 6.5 (s, 1H), 7.12 (s, 5H), 7.6 (dd, 4H), 8.3 (s, 1H). MS: 466 (M+1).

Synthesis of 0122: The compound 0122 was synthesized from 0120 by the same method of synthesis as 0066. Yield: 55% $^1$H NMR (100 MHz, CDCl$_3$), 62.5 (multi, 4H), 2.9 (s, 3H), 3.6 (s, 2H), 3.8 (multi, 4H), 3.85 (s, 3H), 3.9 (s, 3H), 6.6 (s, 1H), 6.7 (multi, 2H), 7.2 (d, 1H), 7.7 (dd, 4H), 8.4 (s, 1H). MS: 526 (M+1).

Synthesis of 0125: 100 mg 0093 was dissolved in 40 ml dry THF. While stirring thoroughly, 120 mg 3-chloromethyl benzoic chloride was added, then 100 mg triethylamine was added dropwise over 2 minutes. The reaction was completed in half an hour. Product was extracted with ethyl acetate and washed with water. After the solvent was evaporated the residue was dissolved in 2 ml of morpholine. This solution was stirred at 60° C. for 2 hours and water was added. Product was extracted with ethyl acetate and washed with water. After solvent was evaporated, the residue was chromatographed on a column of silica gel to give 0125 100 mg. Yield: 60%. $^1$H NMR (100 MHz, CDCl$_3$), 61.27 (d, 6H), 2.6 (multi, 4H), 3 (multi, 1H), 3.65 (s, 2H), 3.8 (multi, 4H), 6.85 (s, 1H), 7.4 (s, 4H), 7.4-8.0 (multi, 4H), 8.35 (s, 1H). MS: 494 (M+1).

Synthesis of 0126: The compound 0126 was synthesized from 0021 by the same method of synthesis as 0125. Yield: 60%. $^1$H NMR (100 MHz, CDCl$_3$), 62.55 (multi, 4H), 3.6 (s, 2H), 3.8 (multi, 4H), 3.85 (s, 3H), 3.9 (s, 3H), 6.45 (s, 1H), 6.6 (multi, 2H), 7.25 (d, 1H), 7.4-8.0 (multi, 4H), 8.25 (s, 1H). MS: 512 (M+1).

Synthesis of 0128: The compound 0128 was synthesized from 0093 by the same method of synthesis as 0080. Yield: 80%. $^1$H NMR (100 MHz, CDCl$_3$), 61.26 (d, 6H), 3.0 (multi, 1H), 7.02 (s, 1H), 7.35 (s, 4H), 7.8 (s, 1H), 8.7 (s, 1H), 9.0 (s, 1H), 9.2 (s, H), 9.4 (s, 1H). MS: 396 (M+1).

Synthesis of 0135: The compound 0135 was synthesized from 0104 by the same method of synthesis as 0080. Yield: 82%. $^1$H NMR (100 MHz, CDCl$_3$) δ4.1 (s, 2H), 6.7 (s, 1H), 7.25 (s, 5H), 7.6 (d, 1H), 8.4 (dd, 1H), 8.7 (s, 1H), 8.9 (d, 1H), 9.2 (s, 1H). MS: 299 (M+1).

Synthesis of 0136: 100 mg 0104 was dissolved in 40 ml dry THF. While stirring thoroughly, 120 mg 3-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of N-methyl piperazine. This solution was stirred at 60° C. for 2 hours and water was added. Product was extracted with ethyl acetate and washed with water. After solvent was evaporated, the residue was chromatographed on a column of silica gel to give 0136 115 mg Yield: 70%. $^1$HNMR (100 MHz, CD$_3$OD) δ4.1 (s, 2H), 6.7 (s, 1H), 7.25 (s, 5H), 7.6 (d, 1H), 8.4 (dd, 1H), 8.7 (s, 1H), 8.9 (d, 1H), 9.2 (s, 1H). MS: 479 (M+1).

Synthesis of 0137: 100 mg 0104 was dissolved in 40 ml dry THF. While stirring thoroughly, 120 mg 3-chloromethyl benzoic chloride was added, then 100 mg triethylamine was added dropwise over 2 minutes. The reaction was completed in half an hour. Product was extracted with ethyl acetate and washed with water. After the solvent was evaporated the residue was dissolved in 2 ml morpholine. This solution was stirred at 60° C. for 2 hours and water was added. Product was extracted with ethyl acetate and washed with water. After solvent was evaporated, the residue was chromatographed on a column of silica gel to give 0137 130 mg Yield: 75%. $^1$H NMR (100 MHz, CD$_3$OD) δ2.4 (s, 3H), 2.6 (s, 8H), 3.6 (s, 2H), 5.05 (s, 2H), 6.5 (s, 1H), 7.35 (s, 5H), 7.4-8.0 (multi, 4H), 8.2 (s, 1H). MS: 466 (M+1).

Synthesis of 0211: 50 mg (0.16 mmol) 0021 was dissolved in 20 ml dry DMF. While thoroughly stirring, 50 mg (0.2 mmol) 3,5-bis-trifluoromethyl-phenyl isocyanate was added. The reaction was completed in half an hour and the product was purified by a column of silica gel to give 73 mg (0.13 mmol, 77%) 0211. $^1$H NMR (100 MHz, CDCl$_3$) δ3.67 (s, 3H), 3.75 (s, 3H),), 6.4 (s, 1H), 6.52 (multi, 3H),), 7.23 (d, 1H), 7.47 (s, 1H), 7.52 (s, 2H), 8.74 (s, 1H), 9.2 (s, 1H). MS: 564 (M+1).

Synthesis of 0212: 50 mg (0.16 mmol) 0021 was dissolved in 20 ml dry DMF. While thoroughly stirring, 55 mg (0.2 mmol) p-toluenesulfonyl isocyanate was added. The reaction was completed in half an hour and the product was purified by a column of silica gel to give 60 mg (0.12 mmol, 75%) 0212. $^1$H NMR (100 MHz, CDCl$_3$) δ2.21 (s, 3H), 3.68 (s, 3H), 3.73 (s, 3H), 6.397 (s, 1H), 6.45 (s, 1H), 6.5 (d, J=9.2, 1H), 6.97 (d, J=8, 2H), 7.73 (d, J=8, 2H), 7.95 (d, J=8, 1H), 9.8 (s, 1H), MS: 506 (M+1).

Synthesis of 0213: 50 mg (0.16 mmol) 0021 was dissolved in 20 ml dry DMF. While thoroughly stirring, 32 mg (0.2 mmol) 3,5-difluorophenyl isocyanate was added. The reaction was completed in half an hour and the product was purified by a column of silica gel to give 45 mg (0.10 mmol, 60%) 0213. $^1$H NMR (100 MHz, CDCl$_3$) δ3.67 (s, 3H), 3.71 (s, 3H), 6.38 (mult, 2H), 6.44 (s, 1H), 6.66 (mult, 1H), 6.66 (mult, 1H), 7.14 (d, 1H), 7.60 (mult, 1H), 8.16 (s, 1H), 9.06 (s, 1H), MS: 464 (M+1).

Synthesis of 0214: 50 mg (0.16 mmol) 0021 was dissolved in 20 ml dry DMF. While thoroughly stirring, 45 mg (0.2 mmol) 3,5-difluorophenyl isocyanate isothiocyanate was added. The reaction was completed in half an hour and the product was purified by a column of silica gel to give 40 mg (0.08 mmol, 50%) 0212. $^1$H NMR (100 MHz, CDCl$_3$) δ3.72 (s, 3H), 3.752 (s, 3H), 6.37 (s, 1H), 6.42 (d, 1H), 6.72 (mult, 2H), 7.02 (mult, 1H), 7.16 (d, 1H), 7.53 (mult, 1H), 7.45 (mult, 1H), 8.12 (s, 1H), 9.35 (s, 1H), MS: 480 (M+1).

Synthesis of 0215: 50 mg (0.16 mmol) 0021 was dissolved in 20 ml dry DMF. While thoroughly stirring, 26 mg (0.2 mmol) methanesulfonyl chloride was added. The reaction was completed in half an hour and the product was purified by a column of silica gel to give 50 mg (0.13 mmol, 70%) 0215. $^1$H NMR (100 MHz, CDCl$_3$) δ2.86 (s, 3H), 3.76 (s, 3H), 3.79 (s, 3H), 6.6 (s, 1H), 6.4-7.3 (multi, 3H), 9.4 (s, 1H).

Synthesis of 0227: Dissolve intermediate 0021 (300 mg, 0.9 mmol) in tetrahydrofuran (20 ml). Add triethylamine (200 mg, 2 mmol), drop phenyl chloroformate (281 mg, 1.8 mmol) at −20° C. into mixture and stir for 2 h. Distill to remove solvent under vacuum. Add dichloromethane (20 ml) and wash with water (20 ml×3). The organic phase was dried with sodium sulfate anhydride. Distill to remove solvent under vacuum. The product 001 (273 mg) was given by column purification with chloroform/methanol. $^1$H-NMR (DMSO-d6): 3.75 (38, s), 3.84 (38, s), 6.63-6.83 (3H, m), 7.20-7.46 (6H, m), 10.10 (1H, s). m/z: 428.05. m.p 204° C.-206° C.

Synthesis of 0228: Dissolve intermediate 0021 (300 mg, 0.9 mmol) in tetrahydrofuran (20 ml). Add triethylamine (300 mg, 3 mmol), drop isobutyl chloroformate (365 mg, 2.7 mmol) at 0° C. into mixture, stir for 1.5 h. Distill to remove solvent under vacuum. Add dichloromethane (20 ml) and wash with water (20 ml×3). The organic phase was dried with sodium sulfate anhydride. Distill to remove solvent under vacuum. The product 002 (248 mg) was given by column purification with chloroform/methanol.

'H-NMR (DMSO-d6): 0.92 (6H, d), 1.91 (1H, m), 3.74 (3H, s), 3.82 (3H, s), 3.89 (2H, d), 6.60-6.75 (3H, m), 7.19 (1H, d), 9.35 (1H, s). m/z: 408.08; m.p 226° C.-227° C.

Synthesis of 0229:Dissolve intermediate 0021 (300 mg, 0.9 mmol) in tetrahydrofuran (20 ml). Add triethylamine (181 mg, 1.8 mmol), drop benzyl chloroformate (306 mg, 1.8 mmol) at 20° C. and stir for 1 h. Distill to remove solvent under vacuum. Add dichloromethane (20 ml) and wash with water (20 ml×3). The organic phase was dried with sodium sulfate anhydride. Distill to remove solvent under vacuum. The product 003 (260 mg) was given by column purification with chloroform/methanol. 'H-NMR (DMSO-d6): 3.74 (3H, s), 3.82 (3H, s), 3.89 (2H, s) 6.60-6.75 (3H, m), 7.10-7.90 (6H, m), 9.35 (1H, s). m/z: 442.07; m.p 165° C.-166° C.

Synthesis of 0230:Dissolve intermediate 0021 (300 mg, 0.9 mmol) in tetrahydrofuran (20 ml). Add triethylamine (181 mg, 1.8 mmol), drop ethyl chloroformate (97 mg, 0.9 mmol) at 50° C., stir for 1 h. Distill to remove solvent under vacuum. Add dichloromethane (20 ml) and wash with water (20 ml×3). The organic phase was dried with sodium sulfate anhydride. Distill to remove solvent under vacuum. The product 004 (228 mg) was given by column purification with chloroform/methanol. 'H-NMR (DMSO-d6): 1.25 (3H, m), 3.74 (3H, s), 3.84 (3H, s), 4.17 (2H, m), 6.62-6.76 (3H, m), 7.72 (1H, d), 9.31 (1H, s). m/z: 380.05; m.p 208° C.-210° C.

Synthesis of 0231:Dissolve intermediate 0021 (500 mg, 1.5 mmol) in tetrahydrofuran (20 ml). Add triethylamine (272 mg, 2.7 mmol), drop methyl chloroformate (256 mg, 2.7 mmol) at 30° C. and stir for 30 min. Distill to remove solvent under vacuum. Add dichloromethane (30 ml) and wash with water (20 ml×3). The organic phase was dried with sodium sulfate anhydride. Distill to remove solvent under vacuum. The product 005 (380 mg) was given by column purification with chloroform/methanol. 'H-NMR (DMSO-d6): 3.68 (3H, s), 3.72 (3H, s), 5.82 (3H, s), 6.37-6.80 (3H, m), 7.23 (1H, d), 9.4 (1H, s). m/z: 366.03; m.p 186° C.-188° C.

Synthesis of 0232:Dissolve intermediate 0021 (400 mg, 1.5 mmol) in tetrahydrofuran (20 ml). Add triphosgene (234 mg, 0.8 mmol), drop triethylamine (272 mg, 2.7 mmol) at room temperature and stir for 1 h. Distill to remove 80% solvent under vacuum. Add hydrochloride acid (1 ml) and stir for 5 min. Distill the left solvent. Add dichloromethane (20 ml) and wash with water (20 ml×3). The organic phase was dried with sodium sulfate anhydride. Distill to remove solvent under vacuum. The product 006 (240 mg) was given by column purification with chloroform/methanol. 'H-NMR (DMSO-d6): 3.73 (3H, s), 3.82 (3H, s) 6.22-6.73 (tetrahydro, m), 7.18 (1H, d), 8.31 (1H, s), m/z: 351.03; m.p 245° C.-248° C.

Synthesis of 0233:Dissolve isopropanol (36 mg, 0.6 mmol), triethylamine (61 mg, 0.6 mmol) in dichloromethane (20 ml). Drop triphosgene (180 ml, 0.6 mmol) in dichloromethane (5 ml) at 0° C. Allow the reaction to warm up to room temperature and stir for 30 min. Wash with water (20 ml×3). The organic phase was dried with sodium sulfate anhydride. Distill to remove solvent under vacuum. Add dichloromethane (20 ml) and intermediate 0021 (300 mg, 0.9 mmol). Stir at room temperature for 2 h. Wash with water (20 ml×3). The organic phase was dried with sodium sulfate anhydride. Distill to remove solvent under vacuum. The product 007 (260 mg) was given by column purification with chloroform/methanol. 'H-NMR (DMSO-d6): 1.24 (6H, d), 3.72 (3H, s), 3.81 (3H, s), 4.87 (1H, s), 6.59-7.18 (4H, m), 9.14 (1H, s). m/z: 394.09; m.p 230° C.-232° C.

Synthesis of 0234:Dissolve intermediate 0021 (300 mg, 0.9 mmol) in chloroform (20 ml). Add triethylamine (181 mg, 1.8 mmol), drop allyl chloroformate (216 mg, 1.8 mmol) at room temperature and stir for 1.5 h. Wash with water (20 ml×3). The organic phase was dried with sodium sulfate anhydride. Distill to remove solvent under vacuum. The product 008 (290 mg) was given by column purification with chloroform/methanol. 'H-NMR (DMSO-d6): 3.73 (3H, s), 3.81 (3H, s), 4.61 (2H, d), 5.23 (1H, dd), 5.39 (1H, dd), 5.95 (2H, m), 6.60-7.19 (4H, m), 9.48 (1H, s). m/z: 392.06; m.p 210° C.-212° C.

Synthesis of 0235:Dissolve n-propanol (36 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 30 min. Add dichloromethane (20 ml) and intermediate 0021 (300 mg, 0.9 mmol). Stir at room temperature for 1.5 h. Distill to remove left solvent. Add dichloromethane and wash with water (20 ml×3). The organic phase was dried with sodium sulfate anhydride. Distill to remove solvent under vacuum. The product 009 (285 mg) was given by column purification with chloroform/methanol. 'H-NMR (DMSO-d6): 0.96 (3H, t), 1.61 (2H, m), 3.18 (2H, t), 3.78 (3H, s), 3.84 (3H, s), 6.28-7.50 (4H, m), 9.31 (1H, s). m/z: 394.06; m.p 202° C.-204° C.

Synthesis of 0236:Dissolve 3-methoxyphenol (74.4 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Stir at 40° C. for 1.5 h. Add intermediate 0021 (300 mg, 0.9 mmol). Stir at room temperature for 3.5 h. Distill to remove left solvent. Add dichloromethane (20 ml) and wash with water (20 ml×3). The organic phase was dried with sodium sulfate anhydride. Distill to remove solvent under vacuum. The product 010 (180 mg) was given by column purification with chloroform/methanol. 'H-NMR (DMSO-d6): 3.73 (3H, s), 3.74 (3H, s), 3.83 (3H, s), 6.62-7.23 (8H, m), 9.99 (1H, s). m/z: 458.06; m.p 204° C.-207° C.

Synthesis of 0237:Dissolve n-amyl alcohol (53 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 1 h. Add intermediate 0021 (300 mg, 0.9 mmol). Stir at room temperature for 2.5 h. Distill to remove left solvent. Add dichloromethane (20 ml) and wash with water (20 ml×3). The organic phase was dried with sodium sulfate anhydride. Distill to remove solvent under vacuum. The product 011 (240 mg) was given by column purification with chloroform/methanol. 'H-NMR (DMSO-d6): 0.89 (3H, t), 1.34 (4H, m), 1.61 (2H, t), 3.74 (3H, s), 3.83 (3H, s), 4.09 (2H, t), 6.61-7.21 (4H, m), 9.33 (1H, s). m/z: 422.10; m.p 178° C.-179° C.

Synthesis of 0238:Dissolve tetrahydrofurfuryl benzoate (61 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 30 min. Add intermediate 0021 (300 mg, 0.9 mmol). Stir at room temperature for 2 h. Distill to remove left solvent. Add dichloromethane (20 ml) and wash with water (20 ml×3). The organic phase was dried with sodium sulfate anhydride. Distill to remove solvent under vacuum. The product 012 (243 mg) was given by column purification with chloroform/methanol. 'H-NMR (DMSO-d6): 1.95 (4H, m), 3.77 (3H, s), 3.87 (3H, s), 3.91 (1H, m), 3.93 (2H, d), 4.25 (2H, t), 6.28-6.58 (3H, m), 6.97 (1H, s), 7.18 (1H, d).

m/z: 436.08; m.p 156° C.-158° C.

Synthesis of 0239:Dissolve n-butanol (44 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 1 h. Add intermediate 0021 (300 mg, 0.9 mmol). Stir at room temperature for 2 h. Distill to remove left solvent. Add dichloromethane (20 ml) and wash with water (20 ml×3). The organic phase was dried with sodium sulfate anhydride. Distill to remove solvent under vacuum. The product 013 (280 mg) was given by column purification with chloroform/methanol. 'H-NMR (DMSO-d6): 0.91 (3H, t), 1.38 (2H, m), 1.59 (2H, m), 3.73 (3H, s), 3.82 (3H, s), 4.11 (2H, t), 6.61-7.20 (4H, m), 9.31 (1H, s). m/z: 408.08; m.p 177° C.-178° C.

Synthesis of 0240:Dissolve cyclopentanol (78 mg, 0.9 mmol), triethylamine (90 mg, 0.9 mmol) in tetrahydrofuran (20 ml). Drop triphosgene (270 ml, 0.9 mmol) in tetrahydrofuran (5 ml) at 0° C. Allow the reaction to warm up to room temperature and stir for 1.5 h. Add intermediate 0021 (500 mg, 1.5 mmol). Stir at room temperature for 3 h. Distill to remove left solvent. Add dichloromethane (20 ml) and wash with water (20 ml×3). The organic phase was dried with sodium sulfate anhydride. Distill to remove solvent under vacuum. The product 014 (300 mg) was given by column purification with chloroform/methanol. 'H-NMR (DMSO-d6): 1.56 (2H, s), 1.69 (2H, s), 1.85 (2H, t), 3.72 (3H, s), 3.82 (3H, s), 5.07 (1H, s), 6.61-7.19 (4H, m), 9.16 (1H, s). m/z: 420.08; m.p 228° C.-230° C.

Synthesis of 0241:Dissolve 1-Heptanol (70 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 1.5 h. Add intermediate 0021 (300 mg, 0.9 mmol). Stir at room temperature for 2 h. Distill to remove left solvent. Add dichloromethane (20 ml) and wash with water (20 ml×3). The organic phase was dried with sodium sulfate anhydride. Distill to remove solvent under vacuum. The product 015 (220 mg) was given by column purification with chloroform/methanol. 'H-NMR (DMSO-d6): 0.87 (3H, t), 1.31 (8H, t), 1.59 (2H, t), 3.72 (3H, s), 3.82 (3H, s), 4.09 (2H, t), 6.61-7.20 (4H, m), 9.31 (1H, s). m/z: 450.13; m.p 144° C.-146° C.

Synthesis of 0242:Dissolve chloroethanol (48 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 30 min. Add intermediate 0021 (300 mg, 0.9 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 016 (220 mg) was given by column purification with chloroform/methanol. 'H-NMR (DMSO-d6): 3.72 (3H, s), 3.82 (3H, s), 4.37 (2H, t), 6.61-7.2 1 (4H, m), 9.61 (1H, s). m/z: 414.01; m.p 211° C.-214° C.

Synthesis of 0243:Dissolve 4-chlorophenol (77 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Stir for 30 min at 40° C. Add intermediate 0021 (300 mg, 0.9 mmol). Stir at room temperature for 3.5 h. Distill to remove left solvent. Add dichloromethane (20 ml) and wash with water (20 ml×3). The organic phase was dried with sodium sulfate anhydride. Distill to remove solvent under vacuum. The product 017 (200 mg) was given by column purification with chloroform/methanol. 'H-NMR (DMSO-d6): 3.75 (3H, s), 3.84 (3H, s), 6.48-7.70 (8H, m), 9.53 (1H, s). m/z: 462.01; m.p 233° C.-236° C.

Synthesis of 0244:Dissolve 4-methylphenol (65 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Stir for 1 h at 40° C. Add intermediate 0021 (300 mg, 0.9 mmol). Stir at room temperature for 2 h. Distill to remove left solvent. Add dichloromethane (20 ml) and wash with water (20 ml×3). The organic phase was dried with sodium sulfate anhydride. Distill to remove solvent under vacuum. The product 018 (210 mg) was given by column purification with chloroform/methanol. 'H-NMR (DMSO-d6): 2.20 (3H, s), 3.75 (3H, s), 3.84 (3H, s), 6.61-7.77 (8H, m), 9.43 (1H, s). m/z: 442.04; m.p 260° C.-262° C.

Synthesis of 0245:Dissolve 2-furylmethanol (59 mg, 0.6 mmol), pyridine (56 mg, 0.7 mmol) in tetrahydrofuran (20 ml). Drop triphosgene (180 ml, 0.6 mmol) in tetrahydrofuran (5 ml) at 0° C. Allow the reaction to warm up to room temperature and stir for 30 min. Add intermediate 0021 (300 mg, 0.9 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 019 (235 mg) was given by column purification with chloroform/methanol.

Synthesis of 0246:Dissolve α-phenylethanol (73 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 1.5 h. Add intermediate 0021 (300 mg, 0.9 mmol). Stir at 50° C. for 1 h. Distill to remove left solvent. Add dichloromethane (20 ml) and wash with water (20 ml×3). The organic phase was dried with sodium sulfate anhydride. Distill to remove solvent under vacuum. The product 020 (200 mg) was given by column purification with chloroform/methanol. 'H-NMR (DMSO-d6): 2.94 (2H, t), 3.73 (3H, s), 3.83 (3H, s), 4.30 (2H, t), 6.61-7.31 (9H, m), 9.41 (1H, s). m/z: 456.08; m.p 200° C.-203° C.

Synthesis of 0247:Dissolve 2-thienylmethanol (68 mg, 0.6 mmol), triethylamine (61 mg, 0.6 mmol) in tetrahydrofuran (20 ml). Drop triphosgene (180 ml, 0.6 mmol) in tetrahydrofuran (5 ml) at −20° C. Allow the reaction to warm up to room temperature and stir for 1 h. Add intermediate 0021 (300 mg, 0.9 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 021 (225 mg) was given by column purification with chloroform/methanol. 'H-NMR (DMSO-d6): 3.73 (3H, s), 3.82 (3H, s), 5.34 (2H, s), 6.61-7.57 (7H, m), 9.56 (1H, s). m/z: 448.01; m.p 225° C.-226° C.

Synthesis of 0248:Dissolve 3-hydroxylpyridine (114 mg, 1.2 mmol), triethylamine (120 mg, 1.2 mmol) in tetrahydrofuran (30 ml). Drop triphosgene (360 ml, 1.2 mmol) in tetrahydrofuran (5 ml) at −15° C. Stir for 1.5 h at 40° C. Add intermediate 0021 (600 mg, 1.8 mmol). Stir at 50° C. for 3 h. Distill to remove left solvent. Add dichloromethane (40 ml) and wash with water (20 ml×3). The organic phase was dried with sodium sulfate anhydride. Distill to remove solvent under vacuum. The product 022 (300 mg) was given by column purification with chloroform/methanol. 'H-NMR (DMSO-d6): 3.73 (3H, s), 3.82 (3H, s), 6.23-7.42 (8H, m), 10.23 (1H, s). m/z: 429.05; m.p 176° C.-178° C.

Synthesis of 0249:Dissolve morpholine (52 mg, 0.6 mmol), triethylamine (61 mg, 0.6 mmol) in tetrahydrofuran (20 ml). Drop triphosgene (180 ml, 0.6 mmol) in tetrahydrofuran (5 ml) at 0° C. Allow the reaction to warm up to room temperature and stir for 1 h. Add intermediate 0021 (300 mg, 0.9 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 023 (238 mg) was given by column purification with chloroform/methanol. 'H-NMR (DMSO-d6): 3.43 (4H, t), 3.58 (4H, t), 3.72 (3H, s), 3.82 (3H, s), 6.60-7.20 (4.H, m), 8.23 (1H, s). m/z: 421.08; m.p 226° C.-227° C.

Synthesis of 0250:Dissolve triphosgene (180 ml, 0.6 mmol) in tetrahydrofuran (10 ml). Cool down to 0° C. Add dropwise tetrahydrofuran (20 ml) solution of intermediate 0021 (300 mg, 0.9 mmol) and triethylamine (200 mg, 2 mmol). Stir at 20° C. for 1 h. Add benzylamine (147 mg, 1.4 mmol) and stir at 20° C. for 1 h. Distill to remove left solvent. Add dichloromethane (20 ml) and wash with water (20 ml×3). The organic phase was dried with sodium sulfate anhydride. Distill to remove solvent under vacuum. The product 024 (320 mg) was given by column purification with chloroform/methanol. 'H-NMR (DMSO-d6): 3.72 (3H, s), 3.82 (3H, s), 4.31 (2H, s), 6.61-7.37 (9H, m), 8.39 (1H, s). m/z: 441.08; m.p 249° C.-250° C.

Synthesis of 0251:Dissolve triphosgene (180 ml, 0.6 mmol) in tetrahydrofuran (10 ml). Cool down to 0° C. Add dropwise tetrahydrofuran (20 ml) solution of intermediate 0021 (300 mg, 0.9 mmol) and triethylamine (200 mg, 2 mmol). Allow the reaction to warm up to room temperature and stir for 1 h. Add butylamine (88 mg, 1.4 mmol) and stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 025 (270 mg) was given by column purification with chloroform/methanol. 'H-NMR (DMSO-d6): 0.91 (3H, t), 1.38 (4H, m), 3.08 (2H, t), 3.74 (3H, s), 3.83 (3H, s), 6.61-7.21 (4H, m), 8.22 (1H, s). m/z: 407.10; m.p 247° C.-249° C.

Synthesis of 0252:Dissolve triphosgene (180 ml, 0.6 mmol) in tetrahydrofuran (10 ml). Cool down to 0° C. Add dropwise tetrahydrofuran (20 ml) solution of intermediate 0021 (300 mg, 0.9 mmol) and triethylamine (200 mg, 2 mmol). Warm up to 50° C. and stir for 1 h. Add phenylamine (130 mg, 1.4 mmol) and stir at 50° C. for 1 h. Distill to remove left solvent. Add dichloromethane (20 ml) and wash with water (20 ml×3). The organic phase was dried with sodium sulfate anhydride. Distill to remove solvent under vacuum. The product 026 (300 mg) was given by column purification with chloroform/methanol. 'H-NMR (DMSO-d6): 3.74 (3H, s), 3.83 (3H, s), 6.70-7.50 (9H, m), 8.58 (1H, s), 9.18 (1H, s). m/z: 427.10; m.p 220° C.-222° C.

Synthesis of 0253:Dissolve ethyl mercaptan (37 mg, 0.6 mmol), triethylamine (61 mg, 0.6 mmol) in tetrahydrofuran (30 ml). Drop triphosgene (180 ml, 0.6 mmol) in tetrahydrofuran (5 ml) at −15° C. Allow the reaction to warm up to room temperature and stir for 30 min. Add intermediate 0021 (300 mg, 0.9 mmol). Stir at 50° C. for 1 h. Distill to remove left solvent. Add dichloromethane (20 ml) and wash with water (20 ml×3). The organic phase was dried with sodium sulfate anhydride. Distill to remove solvent under vacuum. The product 027 (220 mg) was given by column purification with chloroform/methanol. 'H-NMR (DMSO-d6): 1.23 (3H, t), 2.87 (2H, m), 3.74 (3H, s), 3.84 (3H, s), 6.62-7.72 (4H, m), 10.39 (1H, s). m/z: 396.01; m.p 200° C.-202° C.

Synthesis of 0254:Dissolve intermediate 0021 (300 mg, 0.9 mmol) in tetrahydrofuran (20 ml). Add triethylamine (181 mg, 1.8 mmol). Add dropwise carbonochloridic acid ethyl ester (194 mg, 1.8 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 004 (228 mg) was given by column purification with chloroform/methanol.

Synthesis of 0255:Dissolve intermediate 0021 (300 mg, 0.9 mmol) in tetrahydrofuran (20 ml). Add triethylamine (181 mg, 1.8 mmol). Add dropwise carbonochloridic acid phenyl ester (281 mg, 1.8 mmol). Stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 001 (273 mg) was given by column purification with chloroform/methanol.

Synthesis of 0256:Dissolve intermediate 0021 (300 mg, 0.9 mmol) in chloroform (20 ml). Add triethylamine (181 mg, 1.8 mmol). Add dropwise carbonochloridic acid propynyl ester (216 mg, 1.8 mmol). Stir at room temperature for 1.5 h. Wash with water (20 ml×3). The organic phase was dried with sodium sulfate anhydride. Distill to remove solvent under vacuum. The product 008 (290 mg) was given by column purification with chloroform/methanol.

Synthesis of 0257:Dissolve triphosgene (180 ml, 0.6 mmol) in tetrahydrofuran (10 ml). Cool down to 0° C. Add dropwise tetrahydrofuran (20 ml) solution of intermediate 0021 (300 mg, 0.9 mmol) and triethylamine (200 mg, 2 mmol). Warm up to room temperature and stir for 1 h. Add N,N-dimethylaminoethanol (88 mg, 1.4 mmol) and stir at room temperature for 1 h. Distill to remove left solvent. Add dichloromethane (20 ml) and wash with water (20 ml×3). The organic phase was dried with sodium sulfate anhydride. Distill to remove solvent under vacuum. The product 025 (270 mg) was given by column purification with chloroform/methanol.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range.

What is claimed is:
1. A compound of the formula I below:

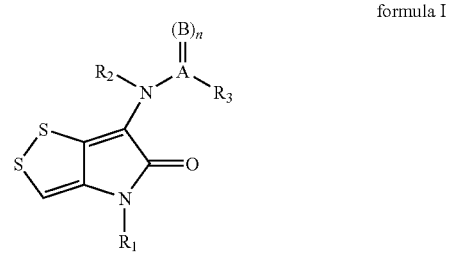

formula I wherein
(a) A is sulfur (S), B is oxygen (O) and n=1 or 2;
R1 and R2 are independently selected from the group consisting of hydrogen, alkyl (C1-C18), aralkyl (C7-C18), cycloalkyl (C3-C18), aryl (C6-C18), and heterocyclic (C3-C18), and R3 is independently selected from the group consisting of hydrogen, aralkyl (C7-C18), cycloalkyl (C3-C18), and heterocyclic (C3-C18); or
(b) A is carbon (C), B is oxygen (O) or sulfur (S) and n=1, R1 and R2 are independently selected from the group consisting of hydrogen, alkyl (C1-C18), aralkyl (C7-C18), cycloalkyl (C3-C18), aryl (C6-C18) and heterocyclic (C3-C18);

R3 is selected from the group consisting of —NR4R5, —OR6 and —NHSO2R6;

R4 and R5 are independently selected from the group consisting of hydrogen, alkyl (C1-C18), aralkyl (C7-C18), cycloalkyl (C3-C18), aryl (C6-C18), and heterocyclic (C3-C18); and R6 is selected from the group consisting of aralkyl (C7-C18), cycloalkyl (C3-C18), aryl (C6-C18) and heterocyclic (C3-C18).

2. The compound of claim 1 wherein A is sulfur (S), B is oxygen (O) and n=1 or 2;

and R1 and R2 are independently selected from the group consisting of hydrogen, alkyl (C1-C18), aralkyl (C7-C18), cycloalkyl (C3-C18), aryl (C6-C18), and heterocyclic (C3-C18), and R3 is independently selected from the group consisting of hydrogen, aralkyl (C7-C18), cycloalkyl (C3-C18), and heterocyclic (C3-C18).

3. The compound of claim 1 wherein, A is carbon (C), B is oxygen (O) or sulfur (S) and n=1;

R1 and R2 are independently selected from the group consisting of hydrogen, alkyl (C1-C18), aralkyl (C7-C18), cycloalkyl (C3-C18), aryl (C6-C18) and heterocyclic (C3-C18);

R3 is selected from the group consisting of —NR4R5, —OR6 and —NHSO2R6;

R4 and R5 are independently selected from the group consisting of hydrogen, alkyl (C1-C18), aralkyl (C7-C18), cycloalkyl (C3-C18), aryl (C6-C18) and heterocyclic (C3-C18); and R6 is selected from the group consisting of aralkyl (C7-C18), cycloalkyl (C3-C18), aryl (C6-C18) and heterocyclic (C3-C18).

4. A compound selected from the group consisting of:
a) 1-(3,5-Bis-trifluoromethyl-phenyl)-3-[4-(2,4-dimethoxy-phenyl)-5-oxo-4,5-dihydro-[1,2]dithiolo[4,3-b]pyrrol-6-yl]-urea;
b) 1-(Toluene-4-sulfonyl)-3-[4-(2,4-dimethoxy-phenyl)-5-oxo-4,5-dihydro-[1,2]dithiolo[4,3-b]pyrrol-6-yl]-urea;
c) 1-(2,4-Difluoro-phenyl)-3-[4-(2,4-dimethoxy-phenyl)-5-oxo-4,5-dihydro-[1,2]dithiolo[4,3-b]pyrrol-6-yl]-urea;
d) [4-(2,4-Dimethoxy-phenyl)-5-oxo-4,5-dihydro-[1,2]dithiolo[4,3-b]pyrrol-6-yl]-carbamic acid phenyl ester;
e) [4-(2,4-Dimethoxy-phenyl)-5-oxo-4,5-dihydro-[1,2]dithiolo[4,3-b]pyrrol-6-yl]-carbamic acid isobutyl ester;
f) [4-(2,4-Dimethoxy-phenyl)-5-oxo-4,5-dihydro-[1,2]dithiolo[4,3-b]pyrrol-6-yl]-carbamic acid benzyl ester;
g) [4-(2,4-Dimethoxy-phenyl)-5-oxo-4,5-dihydro-[1,2]dithiolo[4,3-b]pyrrol-6-yl]-carbamic acid ethyl ester;
h) [4-(2,4-Dimethoxy-phenyl)-5-oxo-4,5-dihydro-[1,2]dithiolo[4,3-b]pyrrol-6-yl]-carbamic acid methyl ester;
i) [4-(2,4-Dimethoxy-phenyl)-5-oxo-4,5-dihydro-[1,2]dithiolo[4,3-b]pyrrol-6-yl]-carbamic acid;
j) [4-(2,4-Dimethoxy-phenyl)-5-oxo-4,5-dihydro-[1,2]dithiolo[4,3-b]pyrrol-6-yl]-carbamic acid isopropyl ester;
k) [4-(2,4-Dimethoxy-phenyl)-5-oxo-4,5-dihydro-[1,2]dithiolo[4,3-b]pyrrol-6-yl]-carbamic acid allyl ester;
l) [4-(2,4-Dimethoxy-phenyl)-5-oxo-4,5-dihydro-[1,2]dithiolo[4,3-b]pyrrol-6-yl]-carbamic acid propyl ester;
m) [4-(2,4-Dimethoxy-phenyl)-5-oxo-4,5-dihydro-[1,2]dithiolo[4,3-b]pyrrol-6-yl]-carbamic acid 4-methoxy-phenyl ester;
n) [4-(2,4-Dimethoxy-phenyl)-5-oxo-4,5-dihydro-[1,2]dithiolo[4,3-b]pyrrol-6-yl]-carbamic acid pentyl ester;
o) [4-(2,4-Dimethoxy-phenyl)-5-oxo-4,5-dihydro-[1,2]dithiolo[4,3-b]pyrrol-6-yl]-carbamic acid pyranylmethyl ester;
p) 4-(2,4-Dimethoxy-phenyl)-5-oxo-4,5-dihydro-[1,2]dithiolo [4,3-b]pyrrol-6-yl]-carbamic acid butyl ester;
q) 4-(2,4-Dimethoxy-phenyl)-5-oxo-4,5-dihydro-[1,2]dithiolo [4,3-b]pyrrol-6-yl]-carbamic acid cyclopentanyl ester;
r) 4-(2,4-Dimethoxy-phenyl)-5-oxo-4,5-dihydro-[1,2]dithiolo [4,3-b]pyrrol-6-yl]-carbamic acid heptyl ester;
s) [4-(2,4-Dimethoxy-phenyl)-5-oxo-4,5-dihydro-[1,2]dithiolo[4,3-b]pyrrol-6-yl]-carbamic acid 2-chlorophenyl ester;
t) [4-(2,4-Dimethoxy-phenyl)-5-oxo-4,5-dihydro-[1,2]dithiolo[4,3-b]pyrrol-6-yl]-carbamic acid 4-chlorophenyl ester;
u) [4-(2,4-Dimethoxy-phenyl)-5-oxo-4,5-dihydro-[1,2]dithiolo[4,3-b]pyrrol-6-yl]-carbamic acid p-tolyl ester;
v) [4-(2,4-Dimethoxy-phenyl)-5-oxo-4,5-dihydro-[1,2]dithiolo[4,3-b]pyrrol-6-yl]-carbamic acid furan-2-ylmethyl ester;
w) [4-(2,4-Dimethoxy-phenyl)-5-oxo-4,5-dihydro-[1,2]dithiolo[4,3-b]pyrrol-6-yl]-carbamic acid phenethyl ester;
x) [4-(2,4-Dimethoxy-phenyl)-5-oxo-4,5-dihydro-[1,2]dithiolo[4,3-b]pyrrol-6-yl]-carbamic acid thiophen-2-ylmethyl ester;
y) [4-(2,4-Dimethoxy-phenyl)-5-oxo-4,5-dihydro-[1,2]dithiolo[4,3-b]pyrrol-6-yl]-carbamic acid pyridin-3-yl ester;
z) 3-[4-(2,4-D imethoxy-phenyl)-5-oxo-4,5-dihydro-[1,2]dithiolo[4,3-b]pyrrol-6-yl]-1,1-bis-(2-hydroxy-ethyl)-urea;
aa) 1-[4-(2,4-D imethoxy-phenyl)-5-oxo-4,5-dihydro-[1,2]dithiolo[4,3-b]pyrrol-6-yl]-3-benzyl-urea;
bb) 1-Butyl-3-[4-(2,4-dimethoxy-phenyl)-5-oxo-4,5-dihydro-[1,2]dithiolo[4,3-b]pyrrol-6-yl]-urea;
cc) 1-[4-(2,4-Dimethoxy-phenyl)-5-oxo-4,5-dihydro-[1,2]dithiolo[4,3-b]pyrrol-6-yl]-3-phenyl-urea;
dd) [4-(2,4-Dimethoxy-phenyl)-5-oxo-4,5-dihydro-[1,2]dithiolo[4,3-b]pyrrol-6-yl]-thiocarbamic acid S-ethyl ester;
ee) 1-(3,5-Difluoro-phenyl)-3-[4-(2,4-dimethoxy-phenyl)-5-oxo-4,5-dihydro-[1,2]dithiolo[4,3-b]pyrrol-6-yl]-thiourea; and
ff) N-[4-(2,4-Dimethoxy-phenyl)-5-oxo-4,5-dihydro-[1,2]dithiolo[4,3-b]pyrrol-6-yl]-methane sulfonamide.

5. A pharmaceutical composition comprising a compound of claim 1 or 4 or a pharmaceutically acceptable salt thereof, in association with a pharmaceutical carrier or diluent.

6. A method of increasing neutrophil production by administering to a subject in need thereof a pharmaceutically effective amount of a compound of claim 1 or 4.

7. A method of preventing or treating neutropenia by administering to a subject in need thereof a pharmaceutically effective amount of a compound of claim 1 or 4.

8. A method of treating a viral, bacterial or fungal infection by administering to a subject in need thereof a pharmaceutically effective amount of a compound of claim 1 or 4.

9. A method of increasing neutrophil production by administering to a subject in need thereof a pharmaceutically effective amount of a compound according to formula I below:

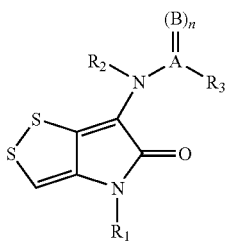

Formula I wherein A is carbon (C), B is oxygen (O) and n=1; and R1, R2 and R3 are independently selected from the group consisting of hydrogen, alkyl (C1-C18), aralkyl (C7-C18), cycloalkyl (C3-C18), aryl (C6-C18) and heterocyclic (C3-C18).

10. A method according to claim 9 wherein said compound is N-[4-(2,4-Dimethoxy-phenyl)-5-oxo-4,5-dihydro-[1,2]dithiolo [4,3-b]pyrrol-6-yl]-3,5-bis-trifluoro methyl-benzamide.

11. A method according to claim 9 wherein said compound is N-[4-(4-Isopropyl-phenyl)-5-oxo-4,5-dihydro-[1,2]dithiolo [4,3-b]pyrrol-6-yl]-3,5-bis-trifluoromethyl-benzamide.

12. A method of preventing or treating neutropenia by administering to a subject in need thereof a pharmaceutically effective amount of N-[4-(2,4-Dimethoxy-phenyl)-5-oxo-4,5-dihydro-[1,2]dithiolo[4,3-b]pyrrol-6-yl]-3,5-bis-trifluoromethyl-benzamide.

* * * * *